US012685806B2

(12) United States Patent
Brozek et al.

(10) Patent No.: US 12,685,806 B2
(45) Date of Patent: Jul. 21, 2026

(54) BLOOD OXYGENATOR WITH AN ORGANIC MEMBRANE

(71) Applicants: SLASKI UNIWERSYTET MEDYCZNY, Katowice (PL); UNIWERSYTET SLASKI, Katowice (PL)

(72) Inventors: Grzegorz Brozek, Katowice (PL); Tomasz Darocha, Dabrowa Gornicza (PL); Jadwiga Gabor, Chorzow (PL); Piotr Knapik, Katowice (PL); Konrad Mendrala, Katowice (PL); Katarzyna Mizia Stec, Katowice (PL); Hubert Okla, Sosnowiec (PL); Mateusz Przyblya, Swietochlowice (PL); Szymon Skoczynski, Swietochlowice (PL); Agnieszka Skoczynska, Ruda Slaska (PL); Arkadiusz Stanula, Zory (PL); Andrzej Swinarew, Myslowice (PL); Ewa Trejnowska, Opole (PL); Michal Zembala, Zbroslawice (PL)

(73) Assignees: UNIWERSYTET SLASKI, Katowice (PL); SLASKI UNIWERSYTET MEDYCZNY, Katowice (PL)

( * ) Notice: Subject to any disclaimer, the term of this patent is extended or adjusted under 35 U.S.C. 154(b) by 490 days.

(21) Appl. No.: 18/254,853

(22) PCT Filed: Nov. 26, 2021

(86) PCT No.: PCT/IB2021/061017
§ 371 (c)(1),
(2) Date: May 27, 2023

(87) PCT Pub. No.: WO2022/113020
PCT Pub. Date: Jun. 2, 2022

(65) Prior Publication Data
US 2024/0001016 A1     Jan. 4, 2024

(30) Foreign Application Priority Data

Nov. 27, 2020   (PL) .......................................... 436123
Nov. 27, 2020   (PL) .......................................... 436124
(Continued)

(51) Int. Cl.
*A61M 1/16*       (2006.01)
*A61M 1/36*       (2006.01)

(52) U.S. Cl.
CPC ........ *A61M 1/1698* (2013.01); *A61M 1/1625* (2014.02); *A61M 1/1629* (2014.02); *A61M 1/3623* (2022.05)

(58) Field of Classification Search
CPC .............. A61M 1/1698; A61M 1/1625; A61M 1/1629; A61M 1/3623; A61M 1/3673;
(Continued)

(56) References Cited

U.S. PATENT DOCUMENTS 4,008,047 A     2/1977   Peterson
4,828,543 A  *  5/1989   Weiss ................... A61M 1/3621
                                                       604/6.11
(Continued)

FOREIGN PATENT DOCUMENTS

DE          3878326 T3     9/1999
EP          0219053 A2  *  4/1987   .......... A61M 1/3673
(Continued)

OTHER PUBLICATIONS

Wang S, Kunselman AR, (Jndar A. Evaluation of Capiox RX25 and Quadrox-i Adult Hollow Fiber Membrane Oxygenators in a Simulated Cardiopulmonary Bypass Circuit. Artif Organs. 2016;40(5):E69-E78. doi: 10.1111/aor.12633, Nov. 2017.
(Continued)

*Primary Examiner* — Rebecca E Eisenberg
*Assistant Examiner* — Brandon W. Levy

(74) *Attorney, Agent, or Firm* — Craft Chu PLLC; Andrew W. Chu

(57) ABSTRACT

The device for blood oxygenation includes a gas exchange chamber with passage openings. One side the chamber is connected in a gas-tight manner with the expansion tank feeding the gas mixture containing oxygen to the chamber, having the inlet opening of gas mixture from the feeding installation. The other side of the chamber is connected in a gas-tight manner with the gas mixture discharging tank, having the outlet opening of gas mixture. The inner part of the chamber has a membrane as a capillary bundle permeable to gas mixture particles and non-permeable to blood particles, ends of which are anchored in the passage openings. The capillary bundle is tensed with a tension force and is parallel to the longitudinal axis of the chamber and to each other, or are arranged spirally. The side wall of the chamber has at least one inlet/outlet opening.

14 Claims, 10 Drawing Sheets

(30) Foreign Application Priority Data

| | | | |
|---|---|---|---|
| Nov. 27, 2020 | (PL) | ........................................ | 436125 |
| Nov. 27, 2020 | (PL) | ........................................ | 436126 |
| Nov. 27, 2020 | (PL) | ........................................ | 436133 |
| Nov. 27, 2020 | (PL) | ........................................ | 436134 |
| Nov. 27, 2020 | (PL) | ........................................ | 436135 |
| Nov. 27, 2020 | (PL) | ........................................ | 436136 |
| Nov. 27, 2020 | (PL) | ........................................ | 436137 |

(58) Field of Classification Search
  CPC ........ A61M 2205/3368; A61M 1/3666; A61M 1/34

See application file for complete search history.

(56) References Cited

U.S. PATENT DOCUMENTS

| | | | | |
|---|---|---|---|---|
| 5,110,548 | A * | 5/1992 | Montevecchi | ...... A61M 1/3621 210/321.78 |
| 5,230,862 | A * | 7/1993 | Berry | .................. B01D 63/027 96/6 |
| 5,263,982 | A * | 11/1993 | Shimomura | .......... B01D 63/04 623/23.65 |
| 5,270,005 | A * | 12/1993 | Raible | ................... A61M 1/267 604/6.14 |
| 6,508,983 | B1 * | 1/2003 | McBurney | .......... A61M 1/1625 604/4.01 |
| 2001/0016729 | A1 * | 8/2001 | Divino, Jr. | .......... A61M 1/3623 604/525 |
| 2008/0014115 | A1 * | 1/2008 | Johns | .................. A61M 1/1678 422/46 |
| 2008/0031773 | A1 * | 2/2008 | Eccleston | .......... A61M 1/3623 604/4.01 |
| 2014/0054227 | A1 * | 2/2014 | Sakurai | ................... A61M 1/34 210/500.33 |
| 2016/0296685 | A1 * | 10/2016 | Wu | ........................ A61M 60/38 |
| 2020/0016312 | A1 | 1/2020 | Galavotti | |
| 2020/0108194 | A1 | 4/2020 | Koelhoffer et al. | |
| 2020/0129687 | A1 | 4/2020 | Knoll et al. | |

FOREIGN PATENT DOCUMENTS

| | | | | |
|---|---|---|---|---|
| EP | 0354959 A1 * | 2/1990 | ......... | B01D 67/0088 |
| EP | 0409496 A2 | 1/1991 | | |
| PL | 165872 B1 | 2/1995 | | |
| PL | 197199 B1 | 3/2008 | | |
| PL | 212620 B1 | 10/2012 | | |
| PL | 225257 B1 | 3/2017 | | |
| WO | 95/34373 A1 | 12/1995 | | |

OTHER PUBLICATIONS

Formica F, Avalli L, Martino A, et al. Extracorporeal membrane oxygenation with a poly-methylpentene oxygenator (Quadrox D). ASAIO J. 2008 ;54( 1) : 89-94. doi: 10.1097/MAT.0b013e31815ff27e.

Clingan S, Schuldes M, Francis S, Hoerr H Jr, Riley J. In vitro elimination of gaseous microemboli utilizing hypobaric oxygenation in the Terumo® FX15 oxygenator. Perfusion. 2016;31(7):552-559. doi:10.1177/0267659116638148.

Gipson KE, Rosinski DJ, Schonberger RB, et al. Elimination of gaseous microemboli from cardiopulmonary bypass using hypobaric oxygenation. Ann Thorac Surg. 2014;97(3):879-886. doi:10.1016/j.athoracsur.2013.08.074.

Ginther RM Jr, Gorney R, Cruz R. A clinical evaluation of the Maquet Quadrox-i Neonatal oxygenator with integrated arterial filter. Perfusion. 2013;28(3):194-199. doi:10.1177/0267659113475694.

* cited by examiner

1

BLOOD OXYGENATOR WITH AN ORGANIC MEMBRANE

CROSS-REFERENCE TO RELATED APPLICATIONS

See also Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The object of the invention is the extracorporeal blood oxygen saturation device (oxygenator for blood oxygenation) and elimination of carbon dioxide from blood, preferably with organic membrane of blowing properties. Extracorporeal blood oxygenation is applied in the conditions of potentially reversible deep lung function disorders to the extent preventing the effective gas exchange using the mechanical ventilation.

2. Description of Related Art Including Information Disclosed Under 37 CFR 1.97 and 37 CFR 1.98

The oxygenator functions as lungs and forms the integral component of cardiopulmonary bypass. Similarly as in the physiological conditions in lungs, the gas exchange process takes place, in which oxygen supplied to the oxygenator chamber replaces blood carbon dioxide. The oxygenator is a device constructed of plenty of thin tubes with blood flowing between them. The tube walls are made of semi-permeable membrane penetrable by gases—oxygen and carbon dioxide, however non-penetrable by blood particles. The space inside the tubes (so called capillaries) is filled with gas mixture, concentration of which is adjustable if needed. Blood flowing between the capillaries releases carbon dioxide and absorbs oxygen particles—this process normally takes place in lungs.

Blood oxygenators and oxygenator materials are well known in the art.

For example, two oxygenators with blood stream flow perpendicular to gas mixture flow are described in the comparative analysis by Wang et al. (2016), according to which the Quadrox-i Adult oxygenator demonstrates low resistance and high biocompatibility with lower pressure drop and lower consumption of hemodynamic energy, while the Capiox RX25 oxygenator demonstrated lower risk of gaseous microemboli (GME) in clinical conditions.

This demonstrates that structural optimisation in order to improve treatment safety is necessary. The circulatory system receives thousands of GME during the ECMO (Extra-Corporeal Membrane Oxygenation) therapy despite the use of membrane oxygenator and arterial filtration. GME result in tissue ischaemia, damage of cerebral and other end organ vascular endothelium, leading to vessel expansion, increased permeability, thrombocyte activation, coagulation cascade and activation of complement and cellular inflammatory mediators. The existing technologies remove GME only partially. It is desirable to develop the systems, which will eliminate the GME production and at the same time maintain good gas exchange parameters [Wang S, Kunselman A R, (Jndar A. Evaluation of Capiox RX25 and Quadrox-i Adult Hollow Fiber Membrane Oxygenators in a Simulated Cardiopulmonary Bypass Circuit. Artif Organs. 2016; 40(5):E69-E78. doi: 10.1111/aor.12633].

According to the experience of Formica et al. (2008), the Quadrox D oxygenator demonstrated the optimum efficiency without plasma leakage and the need to replace ECMO for more than four days in adult patients with cardiogenic shock. The ECMO consisting in the membrane oxygenator with blood stream flow perpendicular to gas mixture flow and with polymethylpentene-modified material and magnetic centrifugal pump was used in the study. The preliminary observations demonstrate that such device with a modified membrane could operate properly for even two weeks. Further modifications of membranes in the oxygenators could lead to improved life span of these devices [Formica F, Avalli L, Martino A, et al. Extracorporeal membrane oxygenation with a poly-methylpentene oxygenator (Quadrox D).

The experience of a single Italian centre in adult patients with refractory cardiogenic shock. ASAIO J. 2008; 54(1): 89-94. doi: 10.1097/MAT.0b013e31815ff27e].

Clingan et al. (2016) performed the studies initiated by Gipson et al. (2014). They applied hypobaric oxygenations to achieve a slight hypoxic state in the Terumo® FX15 oxygenators. Hypobaric oxygenation may decrease the risk related to GME production during the pulsatile flow perfusion, vacuum assisted venous drainage and rapid temperature changes. Similar observations were made by Ginther et al. (2013) during the clinical use of Maquet Quadrox-i neonatal oxygenator. The benefits resulting from low drop of transmembrane pressure were demonstrated [Clingan S, Schuldes M, Francis S, Hoerr H Jr, Riley J. In vitro elimination of gaseous microemboli utilizing hypobaric oxygenation in the Terumo® FX15 oxygenator. Perfusion. 2016; 31(7):552-559. doi:10.1177/0267659116638148; Gipson K E, Rosinski D J, Schonberger R B, et al. Elimination of gaseous microemboli from cardiopulmonary bypass using hypobaric oxygenation. Ann Thorac Surg. 2014; 97(3):879-886. doi:10.1016/j.athoracsur.2013.08.074; Ginther R M Jr, Gorney R, Cruz R. A clinical evaluation of the Maquet Quadrox-i Neonatal oxygenator with integrated arterial filter. Perfusion. 2013; 28(3):194-199. doi: 10.1177/0267659113475694].

The U.S. Pat. No. 4,008,047 discloses the method of fluorouracilation of ethylcellulose which provides good gas permeability and blood compatibility of polymer layers made of the produced fluorinated esters. Fluorouracilled ethylcellulose demonstrates good hydrolytic stability at blood pH and sterilisation conditions (for example 100° C.).

It is used in blood oxygenators, implantable biomedical devices, blood sampling or analysis devices or purification devices, etc. Application of this material for membranes allows for elimination of the coagulation and sterilisation resistance-related issues, however only until the surface layer is used. Wearing down of this layer results in a loss of favourable properties, which is one of the weaknesses of this solution.

The membranes consisting of hollow fibres (capillaries, tubes) are also known in the art. The patent document WO9534373 discloses the semi-permeable membranes with hollow fibres characterized in that they have monofilamentous spacer members distributed spirally or formed on their outer surface. The invention describes also the extracorporeal blood conditioning devices comprising such improved membranes.

Also the organic fluid oxygenators that can be used in particular for oxygenation of blood in the extracorporeal blood circle, without forming the zones, in which fluid flow slows down and stagnates leading to accumulations, thrombi and significantly decreasing the oxygenation capacities are known in the art. The patent document no. US2020016312 discloses the method, in which the oxygenator consists in a container body having a longitudinal axis; a first inlet opening for the oxygen and a second outlet opening for an exhaust gas obtained in the container body; a third inlet opening for an organic fluid to be oxygenated and a fourth outlet opening for oxygenated organic fluid obtained in the container body; an oxygenation chamber of the fluid to be oxygenated that is defined inside the container body; a distribution pre-chamber of the fluid to be oxygenated fitted between the third inlet opening and the oxygenation chamber; capillary fibres that are impermeable to liquids and porous to gasses, designed to enable contact with the organic fluid and arranged inside the oxygenation chamber according with a common parallel direction; dynamic distribution means supported in the distribution pre-chamber by support means. The advantages of the invention include: beneficial ratio between the overall sizes and the oxygenation capacity; prevents slowing down of organic fluid flow and therefore the formation of accumulations and thrombi; prevents crushing of skeins of the capillary hollow fibres, maintaining the intact useful transitional sections and all surfaces of each single "hollow fibre" perfectly permeable and useful, even in the case of a large number of "hollow fibres" per unit of volume.

The patent document no. US2020129687 discloses also the oxygenator comprising the casing and the set of membranes arranged in the casing. The casing has a blood inlet, blood outlet and blood flow path from the blood inlet to blood outlet. The casing defines the central axis and numerous zones arranged concentrically around the central axis. The set of membranes is placed in the casing. The set of membranes comprises the first numerous gas exchange elements arranged in the first casing zone and the second numerous gas exchange elements arranged in the second casing zone. The second zone is arranged concentrically around the first zone, while the zones are smoothly opened towards each other along the body of numerous gas exchange elements and smoothly separated from each other along the distal end. The first zone is configured for smooth connection with the oxygen source, while the second zone is configured for smooth connection with the vacuum pressure source. The blood flow path comprises essentially the radial flow through the first zone to add oxygen to blood, and through the second zone to separate gaseous microemboli from blood by numerous gas exchange elements.

The patent document no. US2020108194 discloses also the method, in which the oxygenator has the integrated air exhaust system, bubbles of which could lead to embolism. The oxygenator comprises the blood inlet and blood outlet. The blood flow path runs from the blood inlet to blood outlet. The blood oxygenator comprises also a gas exchange component located along the blood flow path; a heat exchange component placed along the blood flow path upstream the gas exchange component and one or many porous "hollow fibres" arranged perpendicularly to the blood flow path upstream the heat exchange component.

Many blood oxygenation systems known in the art are constructed in a way that they consist in membranes in the form of capillaries arranged in parallel towards each other however perpendicularly in the direction of blood flow or crossing at the angle of 90° however arranged in a plane perpendicular to the blood flow direction in the device, forming the capillary layer. The gas mixture with oxygen flows through the capillaries. The capillaries are separated from each other and stabilised with the use of spacer members in the form of a system of fibres or nets, most frequently of polyolefins distributed in layers between the membrane (capillary) systems. In addition, each capillary layer can be separated from the adjoining capillary layers with a spacer layer made of fibres in the form of a dense mesh. Through this system, blood is passed perpendicularly to the longitudinal axis of the capillaries (membrane) that is perpendicularly to the flow direction of gas mixture with oxygen in the capillaries. Such system has many disadvantages, including in particular:

effective transfer of oxygen to blood particles requires a relatively high pressure of gas mixture comprising up to nearly 100% of oxygen, which increases the risk of oxidative stress in cells, risk of formation of gas bubbles in blood, which imposes the need to apply the degassing systems, no self-adjustment—despite achieving the absorption capacity, the saturated blood particle continues to be exposed to oxygen, which increases the risk of oxidative stress (release of gas in a form of bubbles to blood after saturation), short contact time of blood particles with an oxygen particle, which results in decreased effectiveness of gas exchange.

The weaknesses of prior art include among others that the form and location of the applied tube (capillary) membranes may affect the coagulation at certain elements and can lead to blood cell hemolysis. The membrane structures comprise sometimes the spacers between the capillaries, which maintain the capillaries in the input positions, which however disturb laminarity of blood flow and lead to formation of turbulent flows, and therefore may promote formation of thrombi and microemboli. The coagulations may lead to infections, organ insufficiencies, primarily kidneys.

The patients with acute respiratory distress syndrome (ARDS) in the period preceding the inclusion of the ECMO extracorporeal blood oxygenation technique are usually subject to aggressive mechanical ventilation with the need to apply ventilation with the use of high pressure of a breathing mixture. Despite the application of lung-saving ventilation protocol, the pressure in respiratory tracts necessary to maintain lung ventilation may damage the areas of pulmonary alveoli not affected by a disease. This leads to barotrauma phenomenon responsible for further secondary lung damage. In addition, severe respiratory failure is also associated with the need to apply high oxygen concentrations for proper tissue oxygenation. The degree of respiratory failure is associated with the need of oxygen demand of high, even nearly 100% oxygen concentration in gas mixture during mechanical pulmonary ventilation with the use of a respirator. Such high oxygen concentration, at the respiratory route, and increased nitrogen resorption from pulmonary alveoli aggravates the existing atelectasis and further impairs the gas exchange. High oxygen concentrations in the breathing mixture lead also to direct damage of type II pneumocytes in pulmonary alveoli. This results in the increasing surfactant deficiencies, the substance coating the inner surface of pulmonary alveoli and preventing their collapse. The surfactant deficiencies cause the extending of the pulmonary areas covered by atelectasis and aggravating pulmonary gas exchange disorders. In addition, the factor aggravating the gas exchange problems of clinical significance in the case of diseases affecting vast majority of interstitial pulmonary tissue, is the physiological hypoxemic pulmonary and bronchial vasospasm, which in the case of processes causing local lung damages is a favourable phenomenon, however in the case of generalised hypoxemia—aggravates the hypoxia symptoms.

These adverse phenomena associated with high, nearly 100% content of oxygen in gas mixture may also take place in the case of extracorporeal oxygenation—ECMO. The need to apply gas mixture of nearly 100% oxygen content supplied to the oxygenator results from technological constrains of a membrane, in which the gas exchange takes place, and which is the main component of the device. The gas exchange surface of a membrane is much less comparing to the pulmonary exchange surface. The surface of alveolar capillaries is circa 70-100 m2, which is much more than in the membranes currently applied in ECMO. Oxygen exchange via a membrane depends to a certain extent from the oxygen partial pressure at both sides of the membrane. In order to ensure maximum membrane capacity, the gas mixture of nearly 100% oxygen content supplied to the oxygenator is used.

Almost pure oxygen is frequently used in treatment with venous-venous or venous-arterial ECMO, contacting with blood morphotic elements, leads to oxidative stress, damage of circulating blood erythrocyte cell membranes. This leads to disintegration of blood cells with release of hemic compounds to blood. Hemolysis leads to anemization of the treated patients.

Also the other blood morphotic components are similarly affected by the harmful high oxygen concentration. Damage to cell membranes of leukocytes and thrombocytes will result in the impaired cellular immunity and decreased capacity of the organism to defend against bacterial and fungal infections as well as induction of a generalised inflammatory reaction and production of prothrombotic factors. Decreased cellular immunity and impaired functions of immunological system affect the effectiveness of treatment of severe pneumonia and sepsis, which are the main indication for venous-venous ECMO. In addition, impaired patient immunity leads to hospitalisation-related infections: vascular bed infection, hematogenous pneumonia, skin infection at the site of drain insertion. Infections during treatment are the second most common complication during ECMO. Therefore, the infections affect the final treatment outcome. There is a need for more frequent and long-term application of broad spectrum antibiotic therapy and therefore generating of antibiotic-resistant bacterial strains. Growing resistance of bacterial strains to antibiotics is a factor increasing the patients' mortality. Thrombocyte damage will result in hypercoaguability (third most common complication), frequently responsible for thromboembolic complications and the need to intensify anticoagulation.

With regard to the above, development of such structure of the device to enable more effective oxygenation and elimination of carbon dioxide at concentrations of used oxygen below 100% at the site, in which the circulating blood is oxygenated in the oxygenator, has become clinically significant. The basis to implement structural changes to the devices known in prior art are physiological phenomena and the observed adaptive mechanisms of healthy lung tissues.

Physiologically in basal metabolic conditions, approx. 6 L/min. flows through the pulmonary bed. In the conditions of increased oxygen demand, such as physical effort or hypermetabolism, for example, during sepsis, the oxygen demand boosts significantly, which is the factor increasing cardiac output and pulmonary ventilation. This allows for increasing blood flow through the pulmonary bed by 2-3 times, reducing the resistance time of an erythrocyte in pulmonary capillaries by approx. 70%, which in effect of expansion of pulmonary capillaries and increasing cardiac output does not affect blood oxygenation (saturation of haemoglobin with oxygen) and pressure in pulmonary bed (in physiological conditions, haemoglobin is fully oxygenated after passing through the erythrocyte of ⅓ of pulmonary capillary length).

On the basis of adaptive mechanisms known in the respiratory physiology and gas exchange in lungs, maximum extension of contact time of erythrocyte with a capillary filled with gas mixture is desirable to effectively oxygenate haemoglobin with the use of the lowest possible oxygen concentration in gas mixture used in the oxygenator.

However, increasing the capillary length alone aiming at the extension of contact type of erythrocyte with a capillary filled with gas mixtures is not a good solution. Technical complications in production and later at the stage of using the device can be encountered, including in particular these associated with maintaining of the desirable parallelism between the capillaries and distances between them and can increase the probability of coagulation of flowing blood. Thus, considering the fact that the capillaries cannot be extended excessively, and their length can still be insufficient for effective gas exchange of gas mixture flowing through it with blood flowing over it, further seeking the concepts of increasing the effectiveness of this exchange has become desirable.

Such method is proposed by the authors of this invention, in which the mechanism ensuring transport of blood flow in parallel to the transport of gas mixture in the capillaries was proposed, in the same or more preferably in the opposite direction, which will enable more effective gas exchange, since it will facilitate the gas exchange process and the resulting oxygen gradient will allow for gradual oxygenation of erythrocytes. Combination of mechanisms in the preferred counter-flow variant, i.e. extension of the actual route of active gas exchange and counter-flow mechanism, will enable significant reduction of the required pressure of gas mixture, which on the basis of pathophysiological and cellular mechanisms should reduce the risk of numerous complications and improve the therapeutic effects.

The additional issue of concern requiring a solution is the selection of relevant materials, of which the individual components of oxygenators are made, including in particular their most important component i.e. the membrane used for blood gas exchange. Such materials should feature primarily so called semi-permeability, which means that they must be permeable to the gas mixture particles and non-permeable to blood particles, however their additional parameters enhancing the performance characteristics is desirable.

The materials of blowing properties used for production of selective membranes that is the membranes permeable only to particles of specific size are known in prior art. Such materials are used to produce among others the membranes utilised for the production of tents, jackets, filters, osmotic membranes, including blood oxygenators.

The most popular, highly technologically advanced—in non-medical applications—blowing material (used for example for jacket production), of which the membranes were produced, is poly (tetrafluoroethylene).

However in medical applications that is for the construction of medical apparatus, there are membranes known in the art, including porous membranes used in the apparatus having a direct contact with the bodily fluids, made of various materials.

For example, the patent document PL225257 reveals the membrane system for local immobilisation of eukaryotic cells, with a support and at least one bi-layer, made sequentially from one layer of polyelectrolyte comprising of polysaccharide hydrogels, including in particular sodium alginate comprising an incorporated fullerenol and protein A in its structure, characterised in that the first layer is applied directly on the group of insulated cells placed then on the support made of the same material in terms of composition and of the second polymer layer made of secondary or tertiary aliphatic amines—comprising of ethylene or methylene groups with incorporated fullerenol. In this system, one layer is applied directly on the group of isolated eukaryotic cells and enables isolation of eukaryotic cells from the outer environment, including in particular microorganisms, at the same time not restricting transport of nutrients through the membrane, allowing for their targeted growth.

The patent document PL212620 reveals the specially modified polyolefin membrane (PP, PE) and the method of modifying the microporous polyolefin membranes intended for insulation of gram (+) bacteria, consisting that the structure of polyolefin membrane of high porosity is entered, using a method known in the art, with polycationic solution, selected from the group comprising of aliphatic amino acids, including protein aminoacids, preferably polar and dissolved in NaCl solution, and then the structure of membrane is entered, using a method known in the art, preferably by drenching, a polyanionic solution, selected from the group comprising of secondary or tertiary amine polymer, including in particular methylamine and ethylamine, preferably comprising 100% of methyl or ethyl groups, dissolved in NaCl solution.

The patent document PL 197199 reveals also the proton-conducting polymer membrane based on hydrated poly (perfluorosulfonic acid) characterized in that it is the reaction product of radiation-induced grafting of poly (perfluorosulfonic acid) with vinylsulfonic acid used in quantity from 1 to 40% w/w or 2-acrylamido-2-methylpropane sulfonic acid used in quantity from 1 to 40% w/w.

The patent document PL165872 reveals the method of producing the multi-layer porous membrane of polytetrafluoroethylene comprising at least two layers with pores of different average diameters, which comprises of the following stages: filling the extruder cylinder with at least two different types of fine-grained polytetrafluoroethylene powders, provided that each of them is mixed with liquid sliding agent.

The patent document EP0409496 reveals the process of producing microporous membranes comprising at least a partially crystalline aromatic polymer comprising the ether or thioether and ketonic bonds in the chain. This process enables production of membranes from certain aromatic polymers of high melting temperature, for example PEDK.

The type of materials of which the membranes were made known from the methods referred to above allows—from steric reasons—their use for blood oxygenation, however their significant biochemical constrains significantly restrict this use. In addition, due to their structure, they are characterized by well-developed surface topography in micrometric scale, which was the reason behind their negative effect on living organisms. At the cellular level, these membranes cause steric damages of cell membranes, which results in cells destabilisation. In addition, the membranes are unable to inhibit thrombi formation and do not prevent against formation of bacterial biofilm.

To this date, the blowing materials used in medical applications included primarily polypropylene (PP) and polyurethane (PU). For example, in the devices used for blood oxygenation process, the porous material used for membrane production was polyurethane, while the material used for construction of components for membrane layers separation (spacer) was polypropylene. Despite high effectiveness of such membranes in terms of gas exchange, they demonstrate the weaknesses associated among others with induced inflammations resulting from low bio-inertia of these materials, which affected the formation of thrombi on the membrane surface, which have been gradually accumulating. In such case, in order to maintain the effectiveness of blood oxygenation, oxygen concentration should be increased, which induces oxidative stress and intensifies the coagulation process, triggering the negative cascade that is gradual boosting of negative factors, since the oxygen concentration needs to be continuously increased to maintain blood saturation level, which intensifies oxidative stress and coagulation. After exceeding a certain threshold, the volume of thrombi is so large that the device becomes inoperable (fails to fulfil its function) and the entire oxygenator system should be replaced.

Various antithrombotic compounds are known in the art. There are fore example albumins-blood proteins produced in the liver responsible for maintenance of oncotic pressure in blood vessels, transport of hardly soluble substances in plasma (fatty acids, certain hormones, calcium ions) and blood buffering. Anti-inflammatory effect of albumins consists in inhibition of leukotriene production by neutrophils and thrombocytes and decreasing the neutrophil sensitivity to inflammatory cytokines. Their antithrombotic effect consists in activation of antithrombine III and inhibition of thrombocyte aggregation.

There are no known oxygenators with membranes of blowing, anti-inflammatory and antithrombotic properties, comprising the immobilised albumin, semi-permeable for gases, while their development has become the additional objective of the authors of this invention.

BRIEF SUMMARY OF THE INVENTION

The object of the invention is the device for blood oxygenation, with a membrane made of an organic material of blowing properties, characterized in that it comprises of a gas exchange chamber of longitudinal shape in a form of a straight cylinder or a elliptic (flattened) cylinder, with passage openings made at its bases, provided that on one side the chamber is connected in a gas-tight manner with the expansion tank feeding the gas mixture containing oxygen to the chamber, having the inlet opening of gas mixture from the feeding installation, and on the other side the chamber is connected in a gas-tight manner with the tank discharging the gas mixture from the chamber, having the outlet opening of gas mixture, and the inner part of the chamber has the membrane in the form of capillary bundle (called also the hollow fibres or tubes) made of a semi-permeable material, that is permeable to gas mixture particles and non-permeable to blood particles, ends of which are anchored in the passage openings in the chamber bases on both sides, the capillaries are tensed with a tension force of a value from 1 to 100 N, preferably 10 N, and are parallel to the longitudinal axis of the chamber and to each other, or in more preferable variant are arranged spirally, that is twisted along the longitudinal axis of the chamber by the same angle falling within the range from 15 to 720 degrees, preferably by the angle from 90 to 360 degrees, in addition the side wall of the chamber near each chamber base has at least one inlet/outlet opening of blood stream, provided that the capillaries forming the membrane have the form of tubes of external diameter from 30 to 600 μm, preferably 100 μm.

Any method of performance of spirally shaped capillaries is allowed, preferably the capillaries are assembled to the bases in the form of straight and parallel to each other tubes, and then are tensed to achieve the relevant tension and the bases are rotated in the opposite directions to achieve twisting of the capillaries by the designed angle, with a view to, at the same time, that the capillary tension remains at the designed level causing no damage to the capillaries.

Preferably, the membrane forming capillaries are made of an organic material of blowing, anti inflammatory and antithrombotic properties consisting in a base in the form of fluoropolymer, preferably polytetrafluoroethylene (PTFE, teflon) or polyvinylidene fluoride (PVDF) or copolymer of hexafluoropropylene and tetrafluoroethylene (FEP) and admixture of albumin embedded in the micro-structure of a base material, in the base admixture ratio from 80÷1 to 1200÷1, preferably 150÷1, provided that the membrane comprises of pores, of which from 40 to 60% are open pores, while the remaining are closed pores, that is filled with active substance in the form of albumin or admixture of argatroban embedded in the microstructure of a base material, in the base admixture ratio from 80÷1 to 1200÷1, preferably 150÷1, provided that the membrane comprises of pores, of which from 40 to 60% are open pores, while the remaining are closed pores, that is filled with active substance in the form of argatroban or admixture of bivalirudin embedded in the microstructure of a base material, in the base admixture ratio from 80÷1 to 1200÷1, preferably 150÷1, provided that the membrane comprises of pores, of which from 40 to 60% are open pores, while the remaining are closed pores, that is filled with active substance in the form of bivalirudin or admixture of fondaparinux dembedded in the microstructure of a base material, in the base admixture ratio from 80÷1 to 1200÷1, preferably 150÷1, provided that the membrane comprises of pores, of which from 40 to 60% are open pores, while the remaining are closed pores, that is filled with active substance in the form of fondaparinux or admixture of heparin embedded in the microstructure of a base material, in the base admixture ratio from 80÷1 to 1200÷1, preferably 150÷1, provided that the membrane comprises of pores, of which from 40 to 60% are open pores, while the remaining are closed pores, that is filled with active substance in the form of heparin.

Preferably, the inlet opening(s) of blood stream to the gas exchange chamber is connected with the blood stream cooler of parameters enabling its cooling down by 0.5-3.5° C., preferably by 2° C., while in a more preferable variant, the outlet opening(s) of blood stream from the gas exchange chamber is connected with a blood stream heating module of parameters enabling its heating to the physiological blood temperature.

Preferably, the Peltier cells are used as the blood stream cooler.

Preferably, the Peltier cells are used as the blood stream heating module.

In the case when the extracorporeal installation is already equipped with the patient blood temperature stabilisation module, the method according to this invention does not need to apply the heating module at the outlet from the gas exchange chamber, while if this installation comprises no patient blood temperature stabilisation module, the method according to the invention is equipped with the heating module, which enables obtaining of physiological blood temperature.

Preferably, the opening(s) placed near the chamber base from the side of tank discharging the gas mixture constitutes the inlet opening of blood stream, while the opening(s) placed near the chamber base from the side of the expansion tank feeding the gas mixture constitutes the outlet opening of blood stream. The specified preferable arrangement of the inlet and outlet openings of blood stream ensures blood flow in the counterflow to the direction of gas mixture flow and therefore the optimum manner of making use of the technical capacity of the method, i.e. maximum blood saturation with oxygen at minimum outside pressure of gas mixture.

In effect of applying the adequate tension force of the capillaries there is no need to use spacers between them to ensure their stability. Such spacers would disturb blood flow laminarity and reduce active surface of gas exchange. Adequate capillary tension will ensure stable position of each of them, which will prevent the viscoelastic effect of capillaries (their vibration) during blood flow. Capillary vibration is undesired since it disturbs blood flow laminarity.

The expansion tank allows to maintain constant pressures of gas mixture at the inlet to each capillary and in the case of obstruction of any capillary, the tank will force automatic pressure increase at the inlet of the remaining capillaries, however within the flow-limited range.

Gas exchange takes place in the chamber that is the oxygen particles are taken from the capillaries transporting the gas mixture and carbon dioxide is taken back to the capillaries.

Preferably, the openings in the chamber bases are arranged in equal distances from each other and symmetrically to each other and at the same time the capillaries anchored in these openings are also arranged in equal distances from each other and symmetrically to each other. Such arrangement of capillaries ensures practically ideal blood flow laminarity. This provides an advantage compared to the methods requiring spaces to maintain constant distance of the hollow fibre tubes (capillaries) between each other.

Preferably, the HEPA filter is assembled at the outlet from the tank discharging the gas mixture, which removes the potential factors that might pose a biological risk from the gas mixture released from the device.

Preferably, the outlet opening of blood stream and outlet opening of blood stream are made in a distance not exceeding 5 mm from a given chamber base.

Preferably, the inlet opening of blood stream is made at the opposite side compared to the outlet opening of blood stream, symmetrically to the chamber's centre of symmetry.

Preferably, on the surface of the inner chamber at its entire length at least to blood stream regulators are assembled symmetrically to the axis of symmetry of the chamber, having the form of longitudinal notches, most preferably of triangular or triangular-like cross-section, provided that in the variant with straight capillaries that is arranged in parallel to the longitudinal axis of the chamber, the regulators are also parallel to the longitudinal axis of the chamber, while in the variant with spiral capillaries the regulators are also arranged spirally, i.e. rotated along the longitudinal axis of the chamber by the same angle falling within the range from 15 to 720 degrees, preferably by an angle equal to the capillary rotation angle. Such regulator layout forces the desired direction—in a preferred variant swirling—of blood flow and at the same time does not disturb blood flow laminarity.

Preferably, the blood outlet opening and/or the blood inlet opening is assembled with densely woven fibre mesh, preferably made of the material identical as the capillary material in a way that the mesh holes have the side from 15 to 100, preferably 38 μm, transverse to the capillaries. Such mesh forms a filter that enables significant increase of protection against penetration of the potential thrombi, and preferably the antithrombotic agent contained in the mesh can lead to self-dissolving of thrombi on the mesh surface. This will constitute a specific automatic thrombus filter cleaning system, which will prevent obstruction of the device with thrombi and penetration of thrombi to the systems downstream of the device in long-term perspective.

Preferably, the outlet channel from the blood outlet opening from the gas exchange chamber is assembled with at least one thrombus filter module, preferably two parallel thrombus filter modules with a by-pass enabling smooth switching that is directing the blood stream to one or the other thrombus filter module interchangeably, provided that in this variant with the thrombus filter module(s) the heating module of blood stream is assembled upstream or more preferably downstream of thrombus filter module(s). The by-pass enables directing the blood stream only through one thrombus filter module, which is operating at the moment, while the other one is a passive module at that time and enables its replacement into the new one without the need to stop the blood flow.

Preferably, upstream of the blood stream cooler which is then fed via the blood inlet opening into the gas exchange chamber, there is at least one thrombus filter module, preferably two parallel thrombus filter modules with a by-pass enabling smooth switching that is directing the blood stream to one or the other thrombus filter module interchangeably Such solution enables directing the blood stream only through one thrombus filter module, which is operating at the moment, while the other one is a passive module at that time and enables its replacement into the new one without the need to stop the blood flow.

In the preferred variant according to the invention, the gas exchange chamber is the swirl chamber, which results from rotation of capillaries by an adequate angle and preferred spiral shape of blood stream regulators placed on the inner walls of the chamber. Ensuring swirling flow of blood stream extends the active route and retention of blood in the chamber, which in turn extends the duration and effectiveness of gas exchange at maintained size parameters of the devices as a whole and minimises the extracorporeal blood volume during the oxygenation process. Due to centrifugal force, the gas exchanges are separated. Heavy particles are pushed away outside that is towards the chamber walls, while light particles are placed inside the blood stream, which increases the effectiveness of gas exchange by minimising multi-directional exchange.

It is proposed to use fibres arranged longitudinally in the blood flow plane intertwined to maximise the active contact surface of blood and fibres, to increase blood flow laminarity and spiral arrangement of fibres will increase diffusion and more effective oxygen and carbon dioxide exchange in accordance with the concentration gradient. At the implementation stage, it is recommended to arrange the fibres in parallel to each other along the longitudinal flow axis and then immobilisation in the bases and rotation of bases against each other by the angle between 90 and 360 degrees, such rotation causes formation of the swirl channel, which is preferred in terms of flow laminarity and exchange effectiveness. Such arrangement will enable lower oxygen pressure and even using the system of lower oxygen concentration and therefore reduced oxidative stress, which in effect results among others in lower blood coagulation on the membrane fibres.

In the proposed method, upstream of the gas exchange chamber, in which the patient blood is oxygenated in the ECMO extracorporeal circulation that is at the blood inlet channel to the gas exchange chamber, there is a blood stream cooler preferably assembled, which enables its cooling by 0.5-3.5° C., preferably by 2° C. Such conditions will be maintained throughout the entire oxygenation process. Reducing the blood stream temperature before its oxygenation will have a positive effect on saturation of haemoglobin with oxygen due to the increased gas solubility in aquatic environment. Application of such method will enable moving the haemoglobin dissociation curve towards left and therefore colder FiO2 in gas mixture fed to the oxygenator. In effect, the use of high, sometimes even nearly 100% content of oxygen in the oxygenating gas mixture will not be necessary. Oxygen content in the mixture can be reduced even to 21%. This will enable reducing the risk of negative effects related to oxidative stress and damage to cell membranes of blood morphotic components. After oxygenation, the patient blood will be preferably heated to physiological temperature. The proposed method will therefore not affect the patient's body temperature, the patient will be maintained in the normothermic state. The method with blood cooling system upstream of oxygenator protects additionally against the increased blood pressure in the installation resulting from higher flow resistances. The pressure will remain at the physiological level.

The materials used for the membrane construction in the preferred embodiment release no chemical compounds toxic to cells and cause no pathogenic reactions in cells.

The membrane constructed of the described materials protects against formation of biofilm (no bacterial plate is formed) due the inner structure of the material that is the system of macromolecules and pores in the material being not the protagonist of bacterial plate development and accumulation.

The chemical structure of macromolecules of the materials used to form the membranes applied in the device according to the invention influences their good blowing properties and at the same time ensures their biocompatibility and bioinertia. The risk of inducing the cellular and humoral inflammatory mediators in the oxygenators is limited and therefore the process of coagulation on the membrane is inhibited. Therefore the risk of secondary multi-organ damage is reduced.

The tests of active substance release capacity (albumin, agratroban, bivaluridin, fondaparinux, heparin) from the membrane used in the method according to the invention were carried out in a flow vessel known in the art with the use of constant volume of polar solvent in the form of ultra-pure water 18.2 MW. The membrane was immersed in the solvent for 30 minutes. Then the solvent was sampled and injected into the flow vessel observing the changes to intrinsic vibration frequency of a disc in the form of crystal oscillator with the applied electrode, in accordance with the Sauerbrey equation, that is the equation connecting the change of vibrations with the change of weight. The disc was placed in a way that the potential sedimentation of the analyte from the solvent causes no false result by gravitational accumulation on the disc. The position of the disc guaranteed that only the weight of absorbed analyte is measured. On the basis of the observed changes to intrinsic vibration frequency of the disk (their decrease), the presence of active substance in the solvent was identified and the agent accumulated on the electrode. This means that when the membrane was immersed in the solvent, the active substance was released from the membrane to the solvent. The experiment was repeated ten times on identical sample and the measurement results were each time similar (within the measurement error). The constancy of changes in time proves the controlled release of active substance from the membrane.

The use of immobilised albumin, agratroban, bivaluridin, fondaparinux or heparin enables maintaining its constant concentration on the contact surface of an element throughout the entire use period of the material (designed product life-cycle). The option of excessive leaching of albumin is minimised and due to the diffusion-controlled release of albumin, its contact concentration on the product surface is constant.

Introduction of albumin to the material, of which the membrane used in the device according to the invention is made provides it also with the desired antithrombotic and anti-inflammatory properties. As already mentioned, albumin has a strong antithrombotic effect for blood and due to its impact on lipids by lipase activation is also used as the antithrombotic agent used for antithrombotic encapsulations. The admixture of albumin is embedded both in the material pores and micro-breaks formed as equilibrium defects at the stage of material formation. This significantly improves the surface continuity of the material structure and therefore protects against accumulation of the organic material in pores and micro-breaks and significantly reduces coagulation. As already mentioned, agratroban has a strong antithrombotic effect for blood and due to its impact on lipids by lipase activation is also used as the antithrombotic agent used for antithrombotic encapsulations. The admixture of agratroban is embedded both in the material pores and micro-breaks formed as equilibrium defects at the stage of material formation. This significantly improves the surface continuity of the material structure and therefore protects against accumulation of the organic material in pores and micro-breaks and significantly reduces coagulation. Introduction of bivaluridin to the material, of which the membrane is made provides it also with the desired antithrombotic and anti-inflammatory properties. As already mentioned, bivaluridin has a strong antithrombotic effect for blood and due to its impact on lipids by lipase activation is also used as the antithrombotic agent used for antithrombotic encapsulations. The admixture of bivaluridin is embedded both in the material pores and micro-breaks formed as equilibrium defects at the stage of material formation. This significantly improves the surface continuity of the material structure and therefore protects against accumulation of the organic material in pores and micro-breaks and significantly reduces coagulation. Introduction of fondaparinux to the material, of which the membrane used in the device according to the invention is made provides it also with the desired antithrombotic and anti-inflammatory properties. As already mentioned, fondaparinux has a strong antithrombotic effect for blood and due to its impact on lipids by lipase activation is also used as the antithrombotic agent used for antithrombotic encapsulations. The admixture of fondaparinux is embedded both in the material pores and micro-breaks formed as equilibrium defects at the stage of material formation. This significantly improves the surface continuity of the material structure and therefore protects against accumulation of the organic material in pores and micro-breaks and significantly reduces coagulation.

Introduction of heparin to the material, of which the membrane is made provides it also with the desired antithrombotic and anti-inflammatory properties. As already mentioned, heparin has a strong antithrombotic effect for blood and due to its impact on lipids by lipase activation is also used as the antithrombotic agent used for antithrombotic encapsulations. The admixture of heparin is embedded both in the material pores and micro-breaks formed as equilibrium defects at the stage of material formation. This significantly improves the surface continuity of the material structure and therefore protects against accumulation of the organic material in pores and micro-breaks and significantly reduces coagulation.

BRIEF DESCRIPTION OF THE SEVERAL VIEWS OF THE DRAWINGS

The object of the invention is explained in detail in the embodiments below and on the drawings.

DETAILED DESCRIPTION OF THE INVENTION

Example 1A

Figure 1:
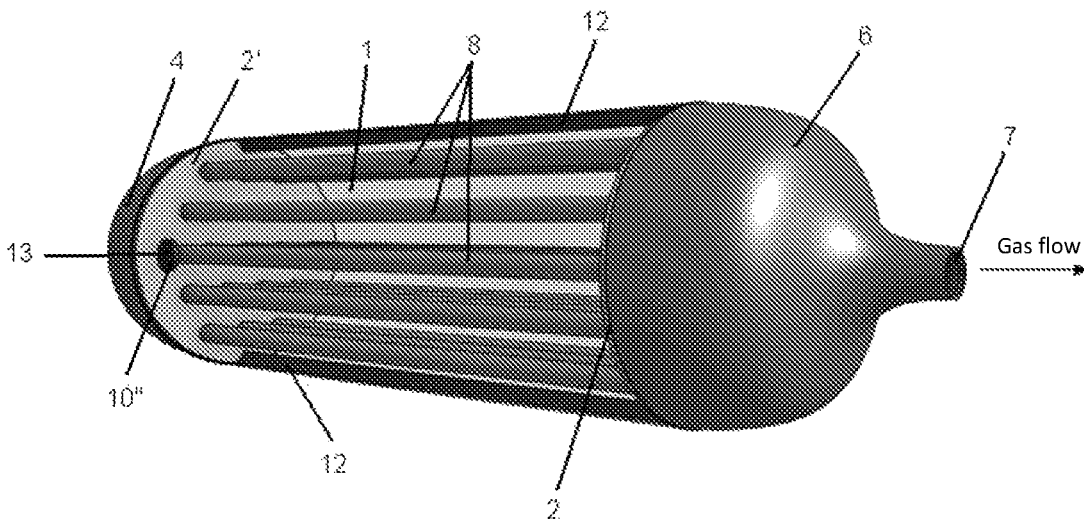
FIG. 1 presents the device for blood oxygenation in axonometric view.
Figure 2:
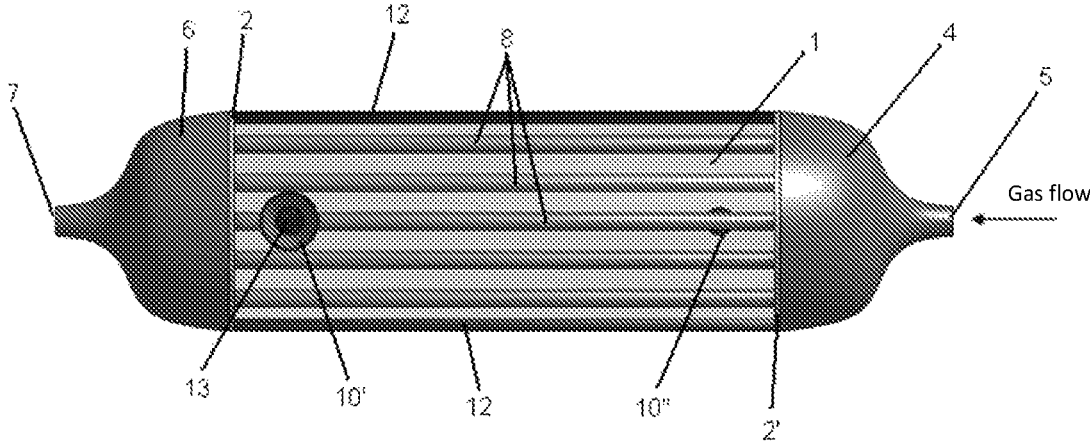
FIG. 2 presents the device for blood oxygenation in a side view, from the side of inlet opening of blood stream.
Figure 3:
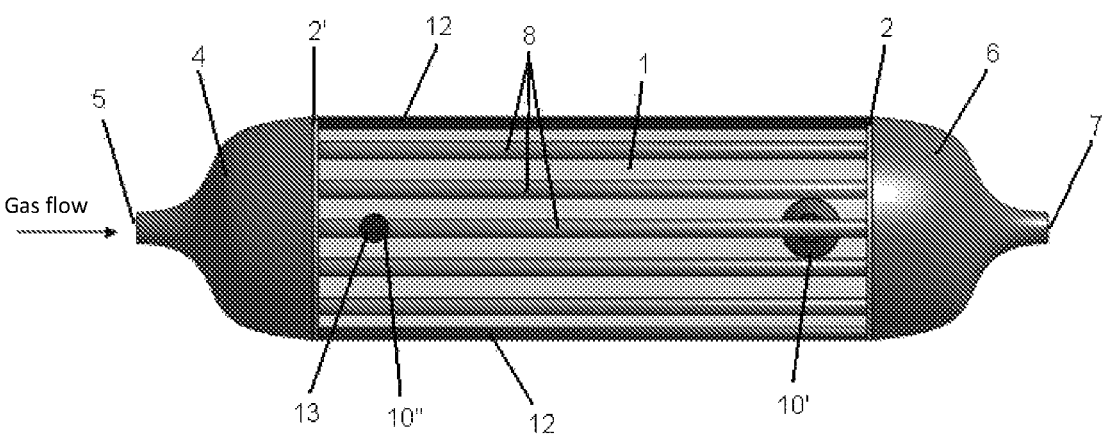
FIG. 3 presents the device for blood oxygenation in a side view, from the side of the outlet opening of blood stream.
Figure 4:
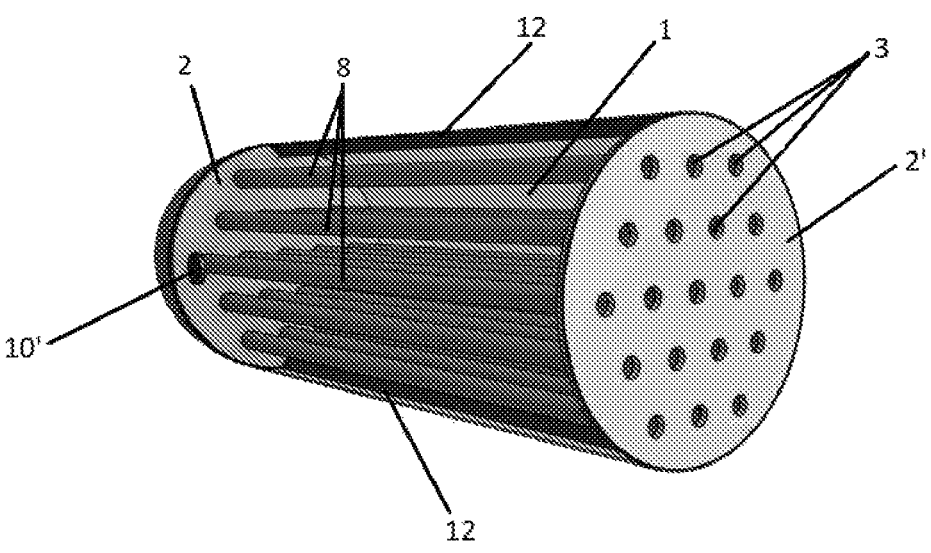
FIG. 4 presents the device for blood oxygenation in axonometric view, in cross-section (after removing the expansion tank), with visible base of gas exchange chamber from the inlet of gas mixture stream.
Figure 5:
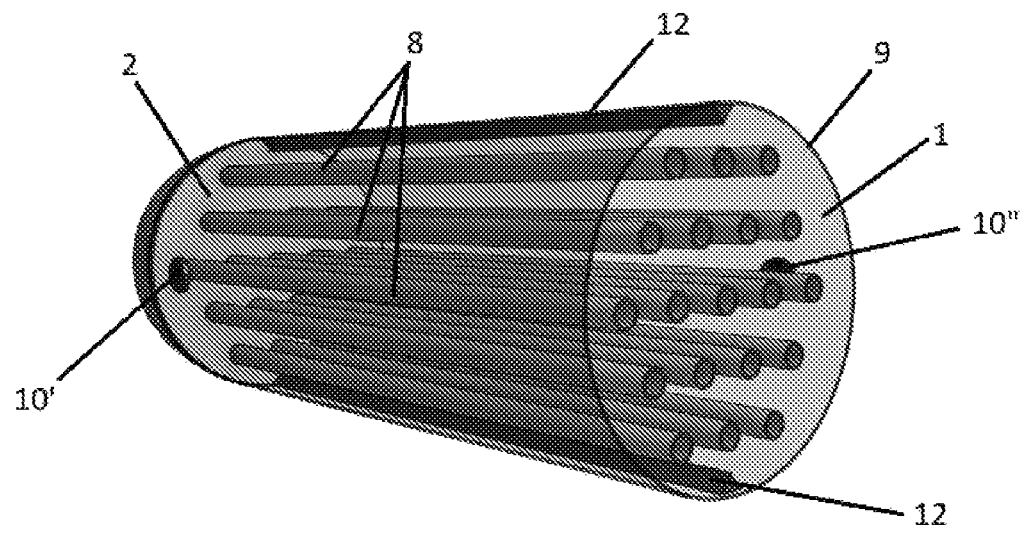
FIG. 5 presents the device for blood oxygenation in axonometric view, in cross-section (after removing the expansion tank and removal of the base of gas exchange chamber from the inlet of gas mixture stream), with visible inlet openings of capillaries.
Figure 6:
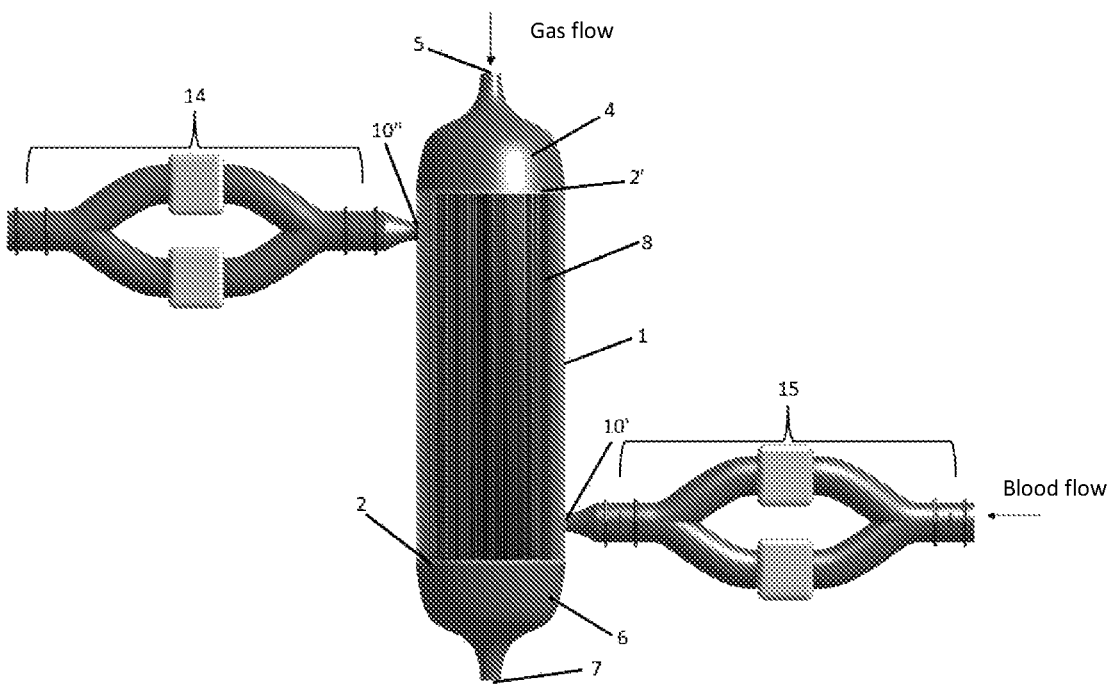
FIG. 6 presents the device for blood oxygenation in top view, in the variant with assembled thrombus filter module, both at the inlet and outlet side of blood stream.
Figure 7:
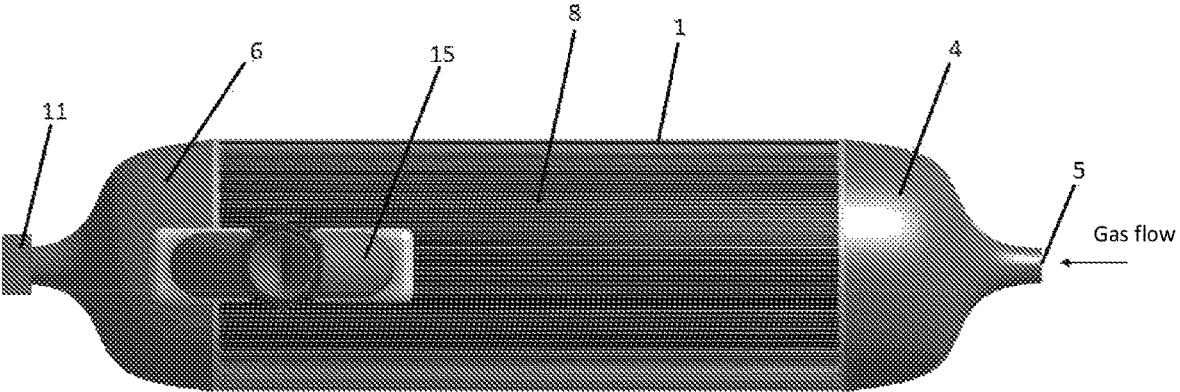
FIG. 7 presents the device for blood oxygenation in a side view, in the variant with thrombus filter module assembled upstream of blood inlet opening to the chamber.
Figure 8:
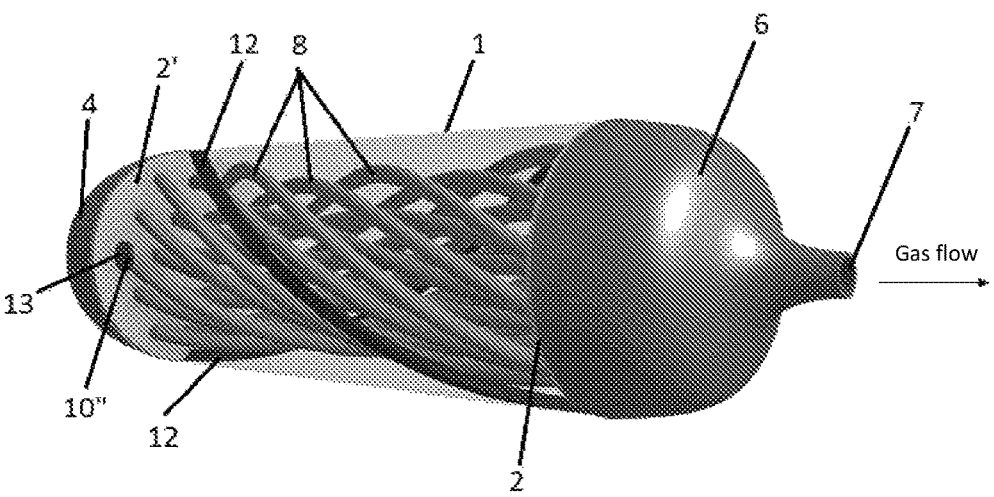
FIG. 8 presents the device for blood oxygenation in axonometric view/
Figure 9:
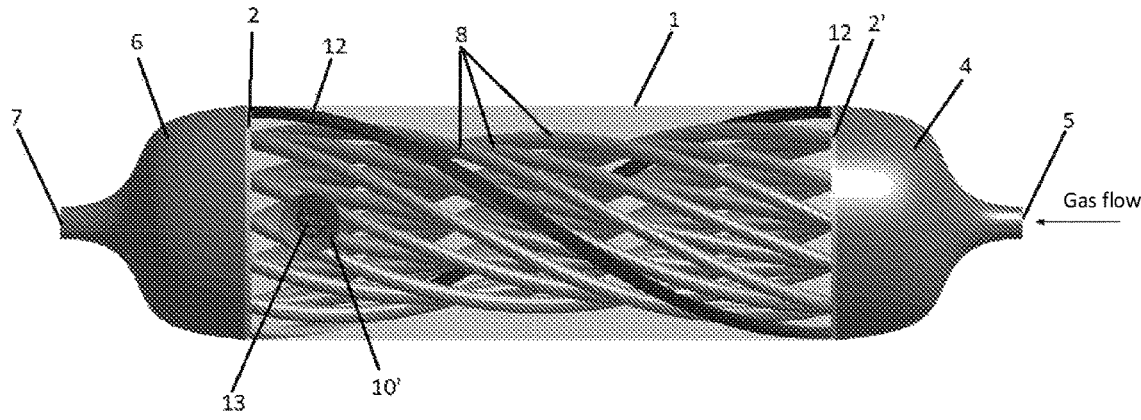
FIG. 9 presents the device for blood oxygenation in a side view, from the side of inlet opening of blood stream.
Figure 10:
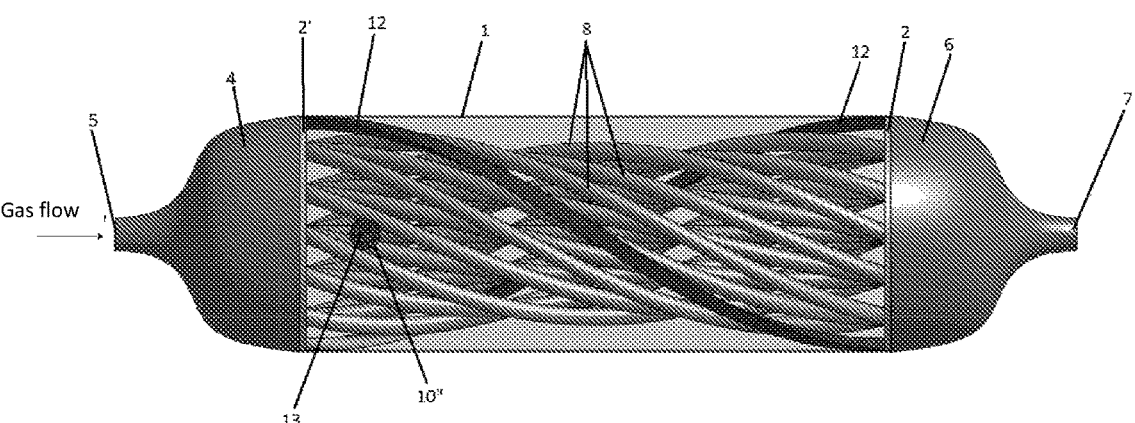
FIG. 10 presents the device for blood oxygenation in a side view, from the side of outlet opening of blood stream.
Figure 11:
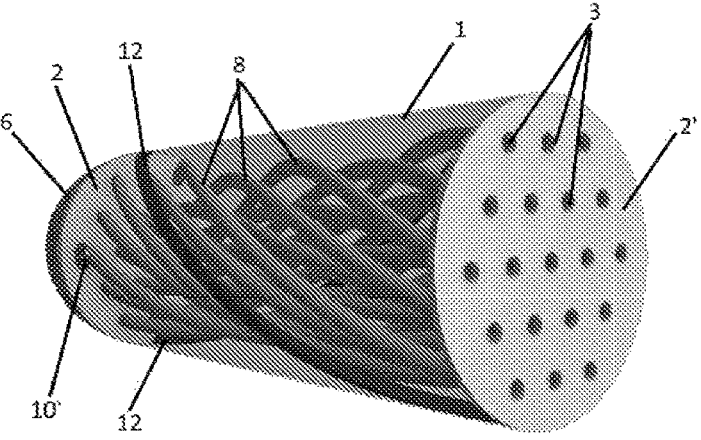
FIG. 11 presents the device for blood oxygenation in axonometric view, in cross-section (after removing the expansion tank), with visible base of gas exchange chamber from the inlet of gas mixture stream.
Figure 12:
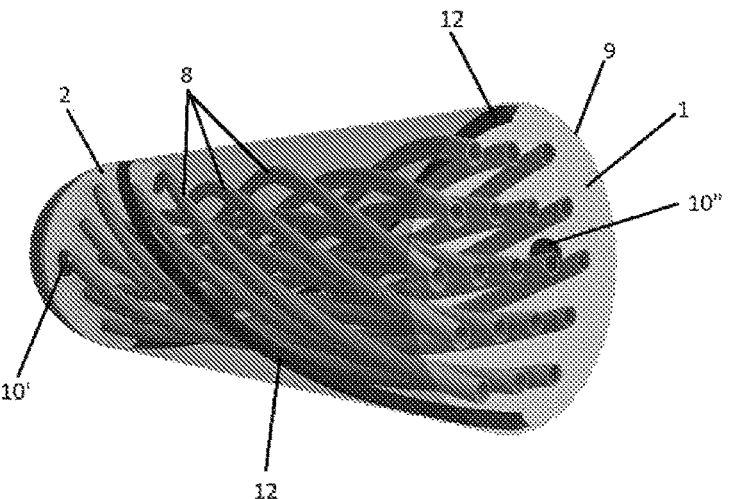
FIG. 12 presents the device for blood oxygenation in axonometric view, in cross-section (after removing the expansion tank and removal of the base of gas exchange chamber from the inlet of gas mixture stream), with visible inlet openings of capillaries.
Figure 13:
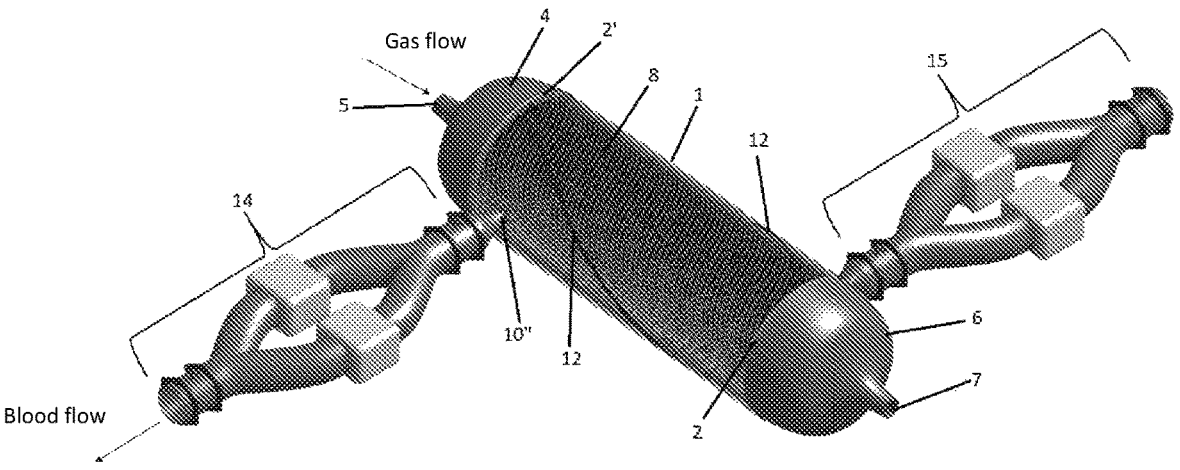
FIG. 13 presents the device for blood oxygenation in top view, in the variant with assembled thrombus filter module both at the inlet and outlet side of blood stream.
Figure 14:
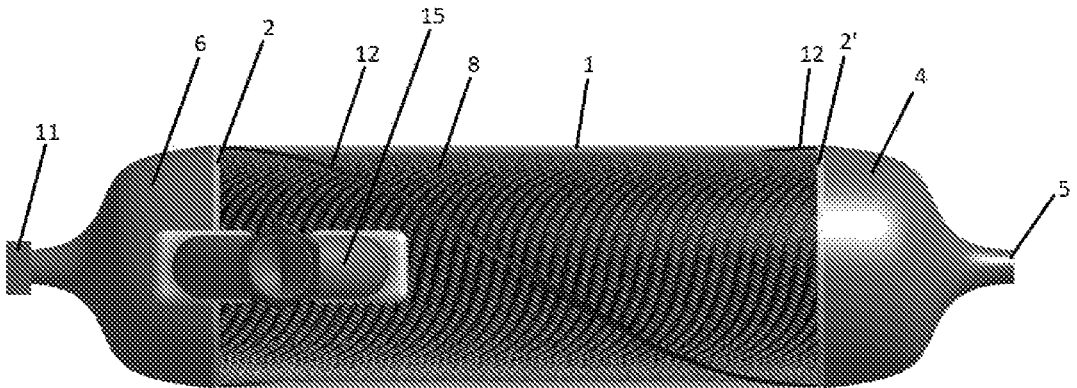
FIG. 14 presents the device for blood oxygenation in a side view, in the variant with thrombus filter module, assembled upstream of the blood inlet opening to the chamber.
Figure 15:
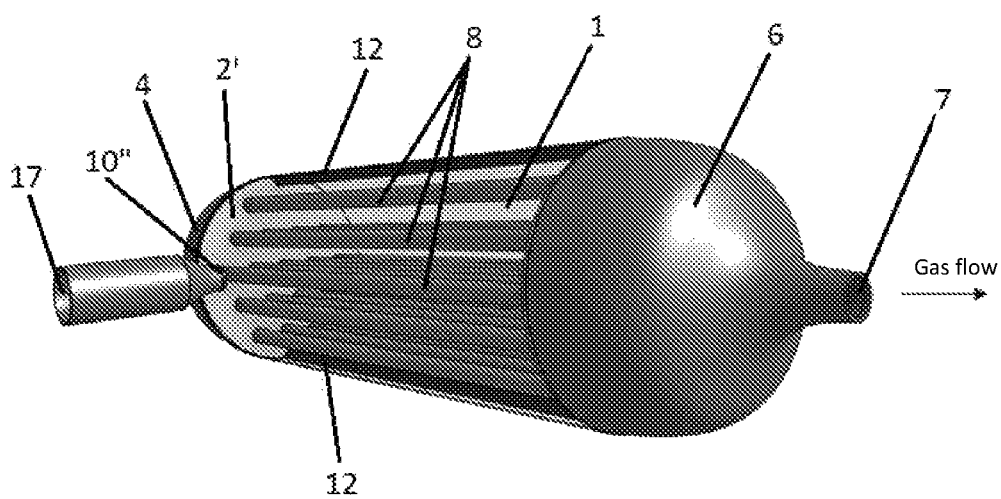
FIG. 15 presents the device for blood oxygenation in axonometric view in a view after the assembly of blood heating module.
Figure 16:
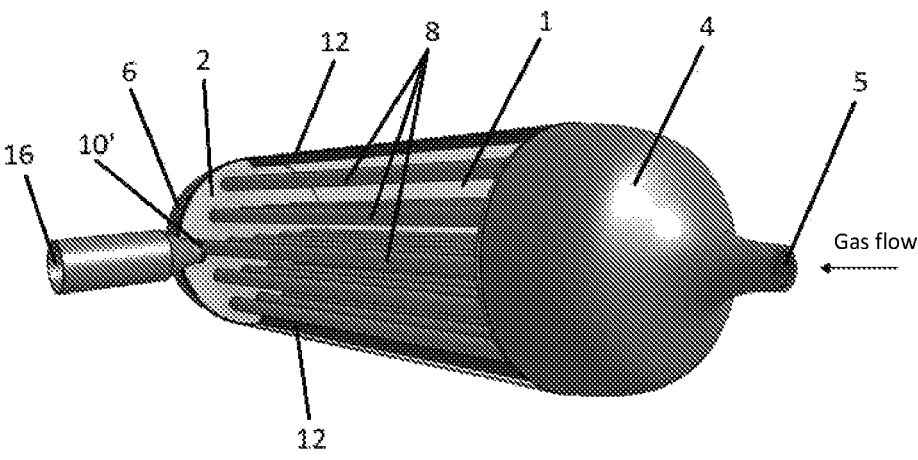
FIG. 16 presents the device for blood oxygenation in axonometric view, in a view after the assembly of a cooler.
Figure 17:
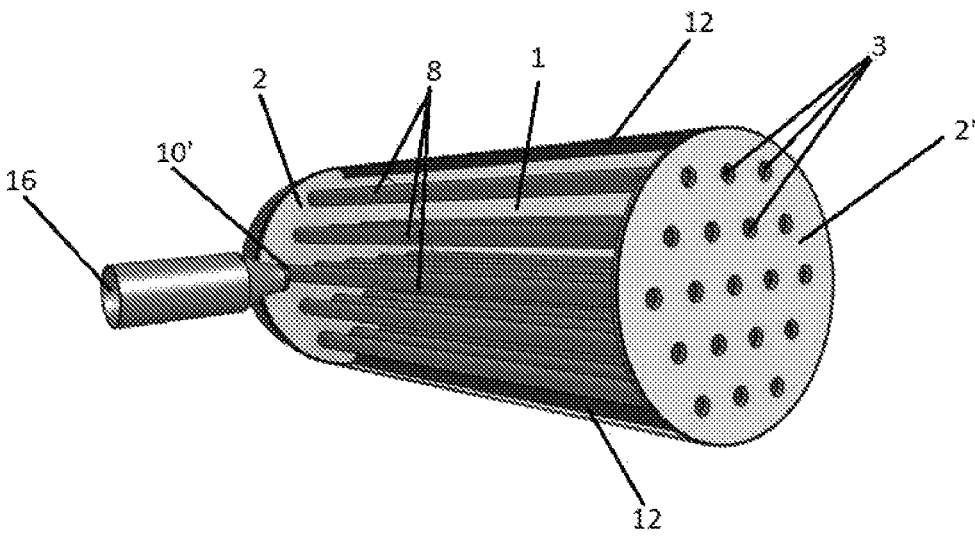
FIG. 17 presents the device for blood oxygenation in axonometric view, after the assembly of a cooler, in cross-section (after removing the expansion tank), with visible base of gas exchange chamber from the side of inlet of gas mixture stream.
Figure 18:
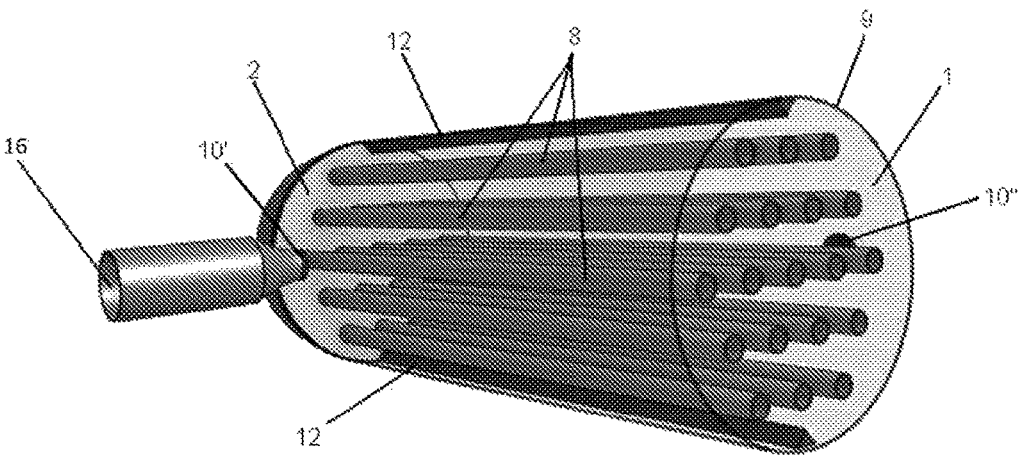
FIG. 18 presents the device for blood oxygenation in axonometric view, after the assembly of a cooler, in cross-section (after removing the expansion tank and removal of the base of gas exchange chamber from the inlet of gas mixture stream), with visible inlet openings of capillaries.
Figure 19:
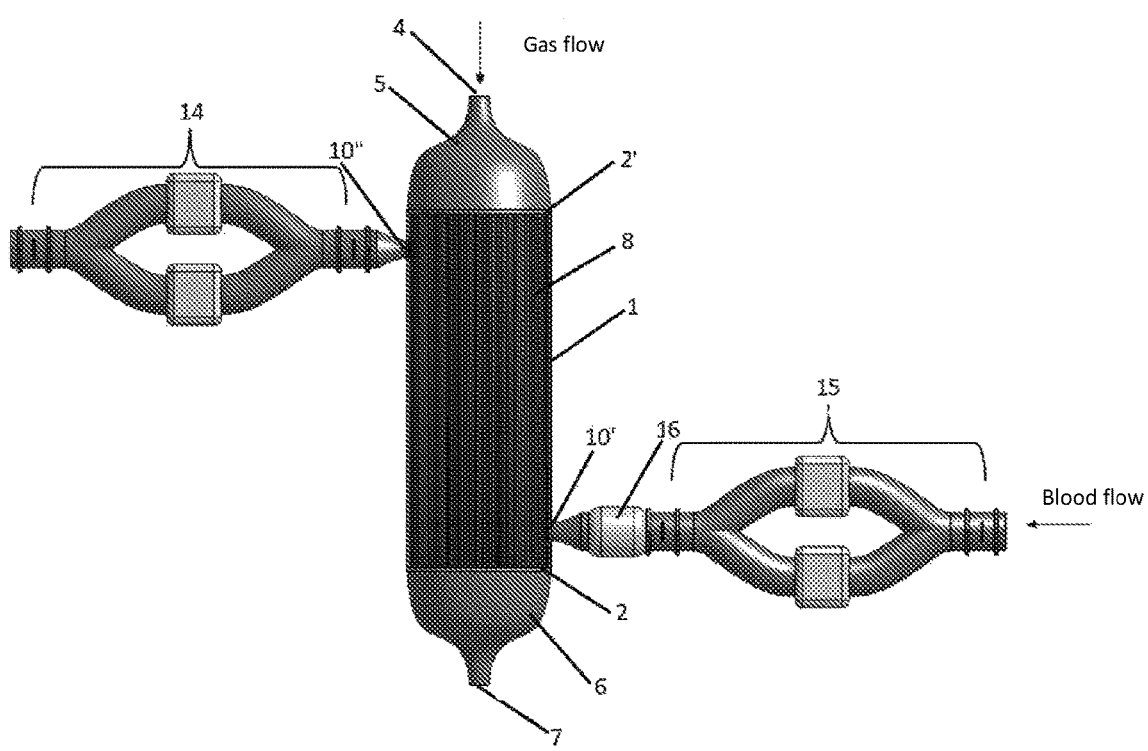
FIG. 19 presents the device for blood oxygenation in top view, in the variant with the assembled thrombus filter module, both at the inlet and outlet side of blood stream and with the installed cooler.
Figure 20:
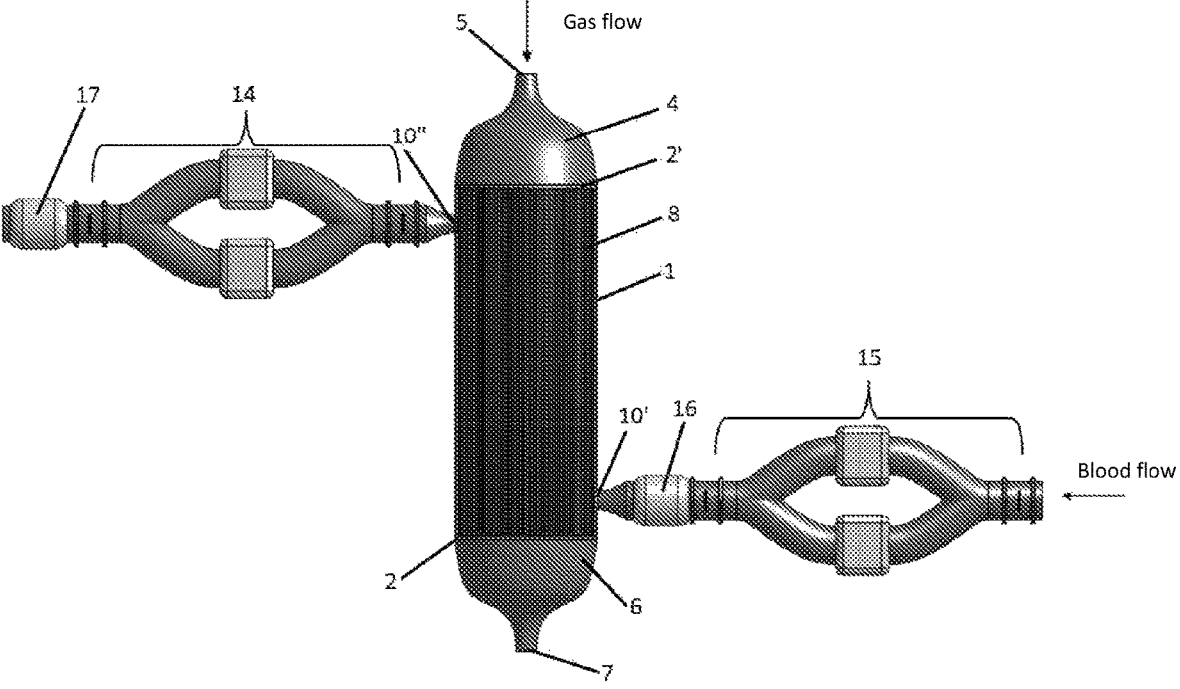
FIG. 20 presents the device for blood oxygenation in top view, in the variant with the assembled thrombus filter module, both at the inlet and outlet side of blood stream, and with the assembled cooler and assembled blood heating module.

The device for blood oxygenation comprising a gas exchange chamber 1 of longitudinal shape in a form of a straight cylinder, with passage openings 3 made at its bases (first base 2, second base 2'), provided that on one side (a first side) the chamber 1 is connected in a gas-tight manner with the expansion tank 4 feeding the gas mixture containing oxygen to the chamber 1, having the inlet opening 5 of gas mixture from the feeding installation on one side along a longitudinal axis of the chamber 1, and on the other side (a second side) the chamber 1 is connected in a gas-tight manner with the gas mixture discharging tank 6 from chamber 1, having the outlet opening 7 of gas mixture along the longitudinal axis of the chamber 1. The inner part of the chamber 1 has the membrane in the form of bundle of capillaries 8 (called also the hollow fibres or tubes) in the form of external diameter of 100 μm made of porous semi-permeable material that is permeable to gas mixture particles and non-permeable to blood particles.

In the preferred embodiment, the material consists of the base in the form of polyethylene terephthalate and admixture of albumin embedded in the micro-structure of a base material, in the base admixture ratio of 1200:1. The membrane comprises of pores, of which 40% are open pores, while the remaining are closed pores, that is filled with active substance in the form of albumin.

In the preferred embodiment, the material consists of the base in the form of PFTE and admixture of agratroban embedded in the micro-structure of a base material, in the base-admixture ratio of 1200:1. The membrane comprises of pores, of which 40% are open pores, while the remaining are closed pores, that is filled with active substance in the form of agratroban.

In the preferred embodiment, the material consists of the base in the form of PFTE and admixture of bivaluridin embedded in the micro-structure of a base material, in the base-admixture ratio of 1200:1.

The membrane comprises of pores, of which 40% are open pores, while the remaining are closed pores, that is filled with active substance in the form of bivaluridin.

In the preferred embodiment, the material consists of the base in the form of copolymer of hexafluoropropylene and tetrafluoroethylene and admixture of fondaparinux embedded in the micro structure of a base material, in the base-admixture ratio of 150:1. The membrane comprises of pores, of which from 40% are open pores, while the remaining are closed pores, that is filled with active substance in the form of fondaparinux.

In the preferred embodiment, the material consists of the base in the form of polyvinylidene fluoride and admixture of heparin embedded in the micro-structure of a base material, in the base-admixture ratio of 150:1. The membrane comprises of pores, of which 40% are open pores, while the remaining are closed pores, that is filled with active substance in the form of heparin.

Ends of capillaries 8 are on both sides anchored (assembled) in passage openings 3 in the bases 2, 2' of chamber 1, while capillaries 8 are arranged spirally, that is twisted along the longitudinal axis of the chamber 1 by the same angle of the value of 360 degrees and tensed with a tension force of a value of 80 N. In the side wall 9 of chamber 1 near the base 2 of chamber 1 from the side of the gas mixture discharging tank 6 there is the blood flow inlet opening 10 of blood stream, while near the base 2 of chamber 1 from the side of the expansion tank 4 feeding the gas mixture there is a blood flow outlet opening 10" of blood stream. The blood flow inlet opening 10' of blood stream and blood flow outlet opening 10" of blood stream are made in a distance of 5 mm from a given base of chamber 1, in addition the blood flow inlet opening 10' of blood stream is made on the opposite side than the blood flow outlet opening 10 of blood stream, symmetrically to the centre of symmetry of chamber 1.

The openings 3 in the bases (first base 2, second base 2') of chamber 1 are arranged in equal distances from each other and symmetrically to each other and at the same time the capillaries 8 anchored in these openings are also arranged in equal distances from each other and symmetrically to each other.

At the outlet from the gas mixture discharging tank 6 the HEPA filter 11 is assembled.

At the surface of the inner chamber, at its entire length, there are two regulators 12 of blood stream assembled symmetrically to the axis of symmetry of chamber 1 having the form of longitudinal notches of triangular cross-section, arranged spirally, that is rotated along the longitudinal axis of chamber 1 by an identical angle equal to the angle of capillary 8 rotation.

At the blood outlet opening 10" the densely woven fibre mesh 13 made of the material identical as the material of capillaries 8 is assembled in a way that the mesh holes have the side of 38 μm, transverse to the capillaries 8.

The inlet opening 10' of blood stream to the gas exchange chamber 1 is connected with a blood stream cooler 16 in the form of Peltier cells, of parameters enabling its cooling by 0.5-3.5° C., preferably by 2° C., while the outlet opening 10" of blood stream from the gas exchange chamber 1 is connected with the blood stream heating module 17 in the form of Peltier cells of parameters enabling its heating to the physiological blood temperature.

Example 1B

The device for blood oxygenation comprising a gas exchange chamber 1 of longitudinal shape in a form of a straight cylinder, with passage openings 3 made at its bases (first base 2, second base 2'), provided that on one side the chamber 1 is connected in a gas-tight manner with the expansion tank 4 feeding the gas mixture containing oxygen to the chamber 1, having the inlet opening 5 of gas mixture from the feeding installation on one side, and on the other side the chamber 1 is connected in a gas-tight manner with the gas mixture discharging tank 6 from chamber 1, having the outlet opening 7 of gas mixture. The inner part of the chamber 1 has the membrane in the form of bundle of capillaries 8 (called also the hollow fibres or tubes) in the form of external diameter of 100 μm made of porous semi-permeable material that is permeable to gas mixture particles and non-permeable to blood particles. The material consists of the base in the form of polyethylene terephthalate. In the preferred embodiment, the material consists of the base in the form of polyethylene terephthalate and admixture of albumin embedded in the micro-structure of a base material, in the base-admixture ratio of 1200:1. The membrane comprises of pores, of which 40% are open pores, while the remaining are closed pores, that is filled with active substance in the form of albumin.

In the preferred embodiment, the material consists of the base in the form of PFTE and admixture of agratroban embedded in the micro-structure of a base material, in the base-admixture ratio of 1200:1. The membrane comprises of pores, of which 40% are open pores, while the remaining are closed pores, that is filled with active substance in the form of agratroban.

In the preferred embodiment, the material consists of the base in the form of PFTE and admixture of bivaluridin embedded in the micro-structure of a base material, in the base-admixture ratio of 1200:1. The membrane comprises of pores, of which 40% are open pores, while the remaining are closed pores, that is filled with active substance in the form of bivaluridin.

In the preferred embodiment, the material consists of the base in the form of copolymer of hexafluoropropylene and tetrafluoroethylene and admixture of fondaparinux embedded in the micro structure of a base material, in the base-admixture ratio of 150:1. The membrane comprises of pores, of which from 40% are open pores, while the remaining are closed pores, that is filled with active substance in the form of fondaparinux.

In the preferred embodiment, the material consists of the base in the form of polyvinylidene fluoride and admixture of heparin embedded in the micro-structure of a base material, in the base-admixture ratio of 150:1. The membrane comprises of pores, of which 40% are open pores, while the remaining are closed pores, that is filled with active substance in the form of heparin.

Ends of capillaries 8 are on both sides anchored (assembled) in passage openings 3 in the bases 2, 2' of chamber 1, while capillaries 8 are arranged spirally, that is twisted along the longitudinal axis of the chamber 1 by the same angle of the value of 360 degrees and tensed with a tension force of a value of 80 N. In the side wall 9 of chamber 1 near the base 2 of chamber 1 from the side of the gas mixture discharging tank 6 there is the inlet opening 10 of blood stream, while near the base 2 of chamber 1 from the side of the expansion tank 4 feeding the gas mixture there is an outlet opening 10" of blood stream. The inlet opening 10' of blood stream and outlet opening 10" of blood stream are made in a distance of 5 mm from a given base of chamber 1, in addition the inlet opening 10' of blood stream is made on the opposite side than the outlet opening 10 of blood stream, symmetrically to the centre of symmetry of chamber 1.

The openings 3 in the bases (first base 2, second base 2') of chamber 1 are arranged in equal distances from each other and symmetrically to each other and at the same time the capillaries 8 anchored in these openings are also arranged in equal distances from each other and symmetrically to each other.

At the outlet from the gas mixture discharging tank 6 the HEPA filter 11 is assembled.

At the surface of the inner chamber, at its entire length, there are two regulators 12 of blood stream assembled symmetrically to the axis of symmetry of chamber 1 having the form of longitudinal notches of triangular cross-section, arranged spirally, that is rotated along the longitudinal axis of chamber 1 by an identical angle equal to the angle of capillary 8 rotation.

At the blood outlet opening 10" the densely woven fibre mesh 13 made of the material identical as the material of capillaries 8 is assembled in a way that the mesh holes have the side of 38 μm, transverse to the capillaries 8.

Example 2

The device for blood oxygenation as in the example 1A, however the rotation angle of capillaries 8 is 720 degrees, while the tension force of capillaries is 100 N, in addition in this variant the method comprises no densely woven fibre mesh 13 assembled on the blood outlet opening 10", however comprises the two parallel thrombus filter modules 14 with a by-pass enabling smooth switching, smooth switching that is directing the blood stream to one or the other thrombus filter module interchangeably, assembled on the outlet channel from the blood outlet opening 10" from gas exchange chamber 1. The thrombus filter modules 14 are assembled between the outlet opening 10" and blood stream heating module 17.

In addition, upstream of the blood stream cooler 16 which is then fed via the blood inlet opening 10' into the gas exchange chamber 1, there are two thrombus filter modules 15 with a by-pass enabling smooth switching that is directing the blood stream to one or the other thrombus filter module interchangeably.

Example 3

The device for blood oxygenation comprising a gas exchange chamber 1 of longitudinal shape in a form of a elliptic cylinder, with passage opening 3 made at its bases (first base 2, second base 2'), provided that on one side the chamber 1 is connected in a gas-tight manner with the expansion tank 4 feeding the gas mixture containing oxygen to the chamber 1, having the inlet opening 5 of gas mixture from the feeding installation on one side, and on the other side the chamber 1 is connected in a gas-tight manner with the gas mixture discharging tank 6 from chamber 1, having the outlet opening 7 of gas mixture. The inner part of the chamber 1 has the membrane in the form of bundle of capillaries 8 (called also the hollow fibres or tubes) in the form of external diameter of 600 μm made of porous semi-permeable material that is permeable to gas mixture particles and non-permeable to blood particles.

In the preferred embodiment, the material consists of the base in the form of PFTE and admixture of albumin embedded in the micro-structure of a base material, in the base-admixture ratio of 80:1. The membrane comprises of pores, of which 40% are open pores, while the remaining are closed pores, that is filled with active substance in the form of albumin.

In the preferred embodiment, the material consists of the base in the form of PFTE and admixture of agratroban embedded in the micro-structure of a base material, in the base-admixture ratio of 1200:1. The membrane comprises of pores, of which 40% are open pores, while the remaining are closed pores, that is filled with active substance in the form of agratroban.

In the preferred embodiment, the material consists of the base in the form of PFTE and admixture of bivaluridin embedded in the micro-structure of a base material, in the base-admixture ratio of 80:1. The membrane comprises of pores, of which 40% are open pores, while the remaining are closed pores, that is filled with active substance in the form of bivaluridin.

In the preferred embodiment, the material consists of the base in the form of polytetrafluoroethylene and admixture of fondaparinux embedded in the micro-structure of a base material, in the base-admixture ratio of 80:1. The membrane comprises of pores, of which 40% are open pores, while the remaining are closed pores, that is filled with active substance in the form of fondaparinux.

In the preferred embodiment, the material consists of the base in the form of polytetrafluoroethylene and admixture of heparin embedded in the micro-structure of a base material, in the base-admixture ratio of 80:1. The membrane comprises of pores, of which 40% are open pores, while the remaining are closed pores, that is filled with active substance in the form of heparin.

Ends of capillaries 8 are on both sides anchored (assembled) in passage openings 3 in the bases 2, 2' of chamber 1, and the capillaries 8 are arranged spirally, that is twisted along the longitudinal axis of the chamber 1 by the same angle of 90 degrees and tensed with tension force of 10 N.

In the side wall 9 of chamber 1 near the base 2 of chamber 1 from the side of the gas mixture discharging tank 6 there is an inlet opening 10' of blood stream, while near the base 2' of chamber 1 from the side of expansion tank 4 feeding the gas mixture there is an outlet opening 10" of blood stream. The inlet opening 10' of blood stream and outlet opening 10" of blood stream are made in a distance of 5 mm from a given base of chamber 1, in addition the inlet opening 10' of blood stream is made on the opposite side than the outlet opening 10 of blood stream, symmetrically to the centre of symmetry of chamber 1.

The openings 3 in the bases (first base 2, second base 2') of chamber 1 are arranged in equal distances from each other and symmetrically to each other and at the same time the capillaries 8 anchored in these openings are also arranged in equal distances from each other and symmetrically to each other.

At the outlet from the gas mixture discharging tank 6 the HEPA filter 11 is assembled.

At the surface of the inner chamber, at its entire length, there are two regulators 12 of blood stream assembled symmetrically to the axis of symmetry of chamber 1 having the form of longitudinal notches of triangular cross-section, arranged spirally, that is rotated along the longitudinal axis of chamber 1 by an identical angle equal to the angle of capillary 8 rotation.

At the blood outlet opening 10" the densely woven fibre mesh 13 made of the material identical as the material of capillaries 8 is assembled in a way that the mesh holes have the side of 20 μm, transverse to the capillaries 8.

The inlet opening 10' of blood stream to the gas exchange chamber 1 is connected with a blood stream cooler 16 in the form of Peltier cells, of parameters enabling its cooling by 0.5-3.5° C., preferably by 2° C., while the outlet opening 10" of blood stream from the gas exchange chamber 1 is connected with the blood stream heating module 17 in the form of Peltier cells of parameters enabling its heating to the physiological blood temperature.

Example 4

The device for blood oxygenation as in the example 1A, however the rotation angle of capillaries 8 is 15 degrees, while the tension force of capillaries is 60 N, in addition in this variant the method comprises no densely woven fibre mesh 13 assembled on the blood outlet opening 10", however comprises the two parallel thrombus filter modules 14 with a by-pass enabling smooth switching, smooth switching that is directing the blood stream to one or the other thrombus filter module interchangeably, assembled on the outlet channel from the blood outlet opening 10 from gas exchange chamber 1. The thrombus filter modules 14 are assembled between the outlet opening 10" and blood stream heating module 17.

In addition, upstream of the blood stream cooler 16 which is then fed via the blood inlet opening 10' into the gas exchange chamber 1, there are two thrombus filter modules 15 with a by-pass enabling smooth switching that is directing the blood stream to one or the other thrombus filter module interchangeably.

Example 5

The device for blood oxygenation as in the example 1A or 1B, however the capillaries 8, of which the membrane consists, have the form of tubes of 100 μm diameter and are made of semi-permeable material, that is permeable to the gas mixture particles and non-permeable to blood particles. The material consists of the base in the form of PVDF and admixture of albumin embedded in the micro-structure of a base material, in the base-admixture ratio of 150:1. The membrane comprises of pores, of which 50% are open pores, while the remaining are closed pores, that is filled with active substance in the form of albumin. In the preferred embodiment, the material consists of the base in the form of PVDF and admixture of agratroban embedded in the micro-structure of a base material, in the base-admixture ratio of 150:1. The membrane comprises of pores, of which 50% are open pores, while the remaining are closed pores, that is filled with active substance in the form of agratroban. In the preferred embodiment, the material consists of the base in the form of PVDF and admixture of bivaluridin embedded in the micro-structure of a base material, in the base-admixture ratio of 150:1. The membrane comprises of pores, of which 50% are open pores, while the remaining are closed pores, that is filled with active substance in the form of bivaluridin. In the preferred embodiment, the material consists of the base in the form of polyvinylidene fluoride and admixture of fondaparinux embedded in the micro-structure of a base material, in the base-admixture ratio of 150:1. The membrane comprises of pores, of which 50% are open pores, while the remaining are closed pores, that is filled with active substance in the form of fondaparinux. In the preferred embodiment, the material consists of the base in the form of copolymer of hexafluoropropylene and tetrafluoroethylene and admixture of heparin embedded in the micro-structure of a base material, in the base-admixture ratio of 150:1. The membrane comprises of pores, of which 50% are open pores, while the remaining are closed pores, that is filled with active substance in the form of heparin.

Example 6

The device for blood oxygenation as in the example 1A or 1B, however the capillaries 8, of which the membrane consists, have the form of tubes of 300 μm diameter and are made of semi-permeable material, that is permeable to the gas mixture particles and non-permeable to blood particles. The material consists of the base in the form of FEP and admixture of albumin embedded in the micro-structure of a base material, in the base-admixture ratio of 80:1. The membrane comprises of pores, of which 60% are open pores, while the remaining are closed pores, that is filled with active substance in the form of albumin. In the preferred embodiment, the material consists of the base in the form of FEP and admixture of agratroban embedded in the micro-structure of a base material, in the base-admixture ratio of 80:1. The membrane comprises of pores, of which 60% are open pores, while the remaining are closed pores, that is filled with active substance in the form of agratroban. In the preferred embodiment, the material consists of the base in the form of FEP and admixture of bivaluridin embedded in the micro-structure of a base material, in the base-admixture ratio of 80:1. The membrane comprises of pores, of which 60% are open pores, while the remaining are closed pores, that is filled with active substance in the form of bivaluridin. In the preferred embodiment, the material consists of the base in the form of polytetrafluoroethylene and admixture of fondaparinux embedded in the micro-structure of a base material, in the base-admixture ratio of 1200:1. The membrane comprises of pores, of which 60% are open pores, while the remaining are closed pores, that is filled with active substance in the form of fondaparinux. In the preferred embodiment, the material consists of the base in the form of polytetrafluoroethylene and admixture of heparin embedded in the micro-structure of a base material, in the base-admixture ratio of 80:1. The membrane comprises of pores, of which 60% are open pores, while the remaining are closed pores, that is filled with active substance in the form of heparin.

Example 7

The device for blood oxygenation as in the example 1A or 1B, however the capillaries 8, of which the membrane consists, have the form of tubes of 150 diameter and are made of semi-permeable material, that is permeable to the gas mixture particles and non-permeable to blood particles. The material consists of the base in the form of PVDF and admixture of albumin embedded in the micro-structure of a base material, in the base-admixture ratio of 200:1. The membrane comprises of pores, of which 60% are open pores, while the remaining are closed pores, that is filled with active substance in the form of albumin. In the preferred embodiment, the material consists of the base in the form of PVDF and admixture of agratroban embedded in the micro-structure of a base material, in the base-admixture ratio of 200:1. The membrane comprises of pores, of which 60% are open pores, while the remaining are closed pores, that is filled with active substance in the form of agratroban. In the preferred embodiment, the material consists of the base in the form of PVDF and admixture of bivaluridin embedded in the micro-structure of a base material, in the base-admixture ratio of 200:1. The membrane comprises of pores, of which 60% are open pores, while the remaining are closed pores, that is filled with active substance in the form of bivaluridin. In the preferred embodiment, the material consists of the base in the form of polyvinylidene fluoride and admixture of fondaparinux embedded in the micro-structure of a base material, in the base-admixture ratio of 150:1. The membrane comprises of pores, of which 60% are open pores, while the remaining are closed pores, that is filled with active substance in the form of fondaparinux. In the preferred embodiment, the material consists of the base in the form of polyvinylidene fluoride and admixture of heparin embedded in the micro-structure of a base material, in the base-admixture ratio of 150:1. The membrane comprises of pores, of which 60% are open pores, while the remaining are closed pores, that is filled with active substance in the form of heparin.

Example 8

The device for blood oxygenation as in the example 1A or 1B, however the capillaries 8, of which the membrane consists, have the form of tubes of 200 μm diameter and are made of semi-permeable material, that is permeable to the gas mixture particles and non-permeable to blood particles. The material consists of the base in the form of FEP and admixture of albumin embedded in the micro structure of a base material, in the base-admixture ratio of 1000:1. The membrane comprises of pores, of which 50% are open pores, while the remaining are closed pores, that is filled with active substance in the form of albumin. In the preferred embodiment, the material consists of the base in the form of FEP and admixture of agratroban embedded in the micro-structure of a base material, in the base-admixture ratio of 1000:1. The membrane comprises of pores, of which 50% are open pores, while the remaining are closed pores, that is filled with active substance in the form of agratroban. In the preferred embodiment, the material consists of the base in the form of FEP and admixture of bivaluridin embedded in the micro-structure of a base material, in the base-admixture ratio of 1000:1. The membrane comprises of pores, of which 50% are open pores, while the remaining are closed pores, that is filled with active substance in the form of bivaluridin. In the preferred embodiment, the material consists of the base in the form of copolymer of hexafluoropropylene and tetrafluoroethylene and admixture of fondaparinux embedded in the micro-structure of a base material, in the base-admixture ratio of 150:1. The membrane comprises of pores, of which from 50% are open pores, while the remaining are closed pores, that is filled with active substance in the form of fondaparinux. In the preferred embodiment, the material consists of the base in the form of polytetrafluoroethylene and admixture of heparin embedded in the micro-structure of a base material, in the base-admixture ratio of 1200:1. The membrane comprises of pores, of which 50% are open pores, while the remaining are closed pores, that is filled with active substance in the form of heparin.

Example 9

The device for blood oxygenation as in the example 1A or 1B, however the capillaries 8, of which the membrane consists, have the form of tubes of 150 μm diameter and are made of semi-permeable material, that is permeable to the gas mixture particles and non-permeable to blood particles. The material consists of the base in the form of PTFE and admixture of albumin embedded in the micro structure of a base material, in the base-admixture ratio of 500:1. The membrane comprises of pores, of which 55% are open pores, while the remaining are closed pores, that is filled with active substance in the form of albumin. In the preferred embodiment, the material consists of the base in the form of PFTE and admixture of agratroban embedded in the micro-structure of a base material, in the base-admixture ratio of 500:1. The membrane comprises of pores, of which 55% are open pores, while the remaining are closed pores, that is filled with active substance in the form of agratroban. In the preferred embodiment, the material consists of the base in the form of PFTE and admixture of bivaluridin embedded in the micro-structure of a base material, in the base-admixture ratio of 500:1. The membrane comprises of pores, of which 55% are open pores, while the remaining are closed pores, that is filled with active substance in the form of bivaluridin. In the preferred embodiment, the material consists of the base in the form of polytetrafluoroethylene and admixture of fondaparinux embedded in the micro-structure of a base material, in the base-admixture ratio of 1200:1. The membrane comprises of pores, of which 55% are open pores, while the remaining are closed pores, that is filled with active substance in the form of fondaparinux. In the preferred embodiment, the material consists of the base in the form of polytetrafluoroethylene and admixture of heparin embedded in the micro-structure of a base material, in the base-admixture ratio of 80:1. The membrane comprises of pores, of which 55% are open pores, while the remaining are closed pores, that is filled with active substance in the form of heparin.

Example 10

The device for blood oxygenation as in the example 1A or 1B, however the capillaries 8, of which the membrane consists, have the form of tubes of 500 μm diameter and are made of semi-permeable material, that is permeable to the gas mixture particles and non-permeable to blood particles. The material consists of the base in the form of PTFE and admixture of albumin embedded in the micro structure of a base material, in the base-admixture ratio of 150:1. The membrane comprises of pores, of which 45% are open pores, while the remaining are closed pores, that is filled with active substance in the form of albumin. In the preferred embodiment, the material consists of the base in the form of PFTE and admixture of agratroban embedded in the micro-structure of a base material, in the base-admixture ratio of 150:1. The membrane comprises of pores, of which 45% are open pores, while the remaining are closed pores, that is filled with active substance in the form of agratroban. In the preferred embodiment, the material consists of the base in the form of PFTE and admixture of bivaluridin embedded in the micro-structure of a base material, in the base-admixture ratio of 150:1. The membrane comprises of pores, of which 45% are open pores, while the remaining are closed pores, that is filled with active substance in the form of bivaluridin. In the preferred embodiment, the material consists of the base in the form of polyvinylidene fluoride and admixture of fondaparinux embedded in the micro-structure of a base material, in the base-admixture ratio of 150:1. The membrane comprises of pores, of which 45% are open pores, while the remaining are closed pores, that is filled with active substance in the form of fondaparinux. In the preferred embodiment, the material consists of the base in the form of polyvinylidene fluoride and admixture of heparin embedded in the micro-structure of a base material, in the base-admixture ratio of 150:1. The membrane comprises of pores, of which 45% are open pores, while the remaining are closed pores, that is filled with active substance in the form of heparin.

Example 11

The device for blood oxygenation as in the example 1A or 1B, however the capillaries 8, of which the membrane consists, have the form of tubes of 150 μm diameter and are made of semi-permeable material, that is permeable to the gas mixture particles and non-permeable to blood particles. The material consists of the base in the form of FEP and admixture of albumin embedded in the micro-structure of a base material, in the base-admixture ratio of 150:1. The membrane comprises of pores, of which 60% are open pores, while the remaining are closed pores, that is filled with active substance in the form of albumin. In the preferred embodiment, the material consists of the base in the form of FEP and admixture of agratroban embedded in the micro-structure of a base material, in the base-admixture ratio of 150:1. The membrane comprises of pores, of which 60% are open pores, while the remaining are closed pores, that is filled with active substance in the form of agratroban. In the preferred embodiment, the material consists of the base in the form of FEP and admixture of bivaluridin embedded in the micro-structure of a base material, in the base-admixture ratio of 150:1. The membrane comprises of pores, of which 60% are open pores, while the remaining are closed pores, that is filled with active substance in the form of bivaluridin. In the preferred embodiment, the material consists of the base in the form of copolymer of hexafluoropropylene and tetrafluoroethylene and admixture of fondaparinux embedded in the micro-structure of a base material, in the base-admixture ratio of 150:1. The membrane comprises of pores, of which from 60% are open pores, while the remaining are closed pores, that is filled with active substance in the form of fondaparinux. In the preferred embodiment, the material consists of the base in the form of copolymer of hexafluoropropylene and tetrafluoroethylene and admixture of heparin embedded in the micro structure of a base material, in the base-admixture ratio of 150:1. The membrane comprises of pores, of which 60% are open pores, while the remaining are closed pores, that is filled with active substance in the form of heparin.

Example 12

The device for blood oxygenation as in the example 1A or 1B, however the capillaries 8, of which the membrane consists, have the form of tubes of 150 μm diameter and are made of semi-permeable material, that is permeable to the gas mixture particles and non-permeable to blood particles. The material consists of the base in the form of PVDF and admixture of albumin embedded in the micro-structure of a base material, in the base-admixture ratio of 100:1. The membrane comprises of pores, of which 50% are open pores, while the remaining are closed pores, that is filled with active substance in the form of albumin. In the preferred embodiment, the material consists of the base in the form of PVDF and admixture of agratroban embedded in the micro-structure of a base material, in the base-admixture ratio of 100:1. The membrane comprises of pores, of which 50% are open pores, while the remaining are closed pores, that is filled with active substance in the form of agratroban. In the preferred embodiment, the material consists of the base in the form of PVDF and admixture of bivaluridin embedded in the micro-structure of a base material, in the base-admixture ratio of 100:1. The membrane comprises of pores, of which 50% are open pores, while the remaining are closed pores, that is filled with active substance in the form of bivaluridin. In the preferred embodiment, the material consists of the base in the form of silicon and admixture of fondaparinux embedded in the micro-structure of a base material, in the base-admixture ratio of 100:1. The membrane comprises of pores, of which 50% are open pores, while the remaining are closed pores, that is filled with active substance in the form of fondaparinux. In the preferred embodiment, the material consists of the base in the form of polyvinylidene fluoride and admixture of heparin embedded in the micro-structure of a base material, in the base-admixture ratio of 150:1. The membrane comprises of pores, of which 50% are open pores, while the remaining are closed pores, that is filled with active substance in the form of heparin.

Example 13

The device for blood oxygenation, as in the example 1A or 1B, or 2, or 3, or 4, provided that the membrane has straight capillaries instead of spiral capillaries, that is parallel to the longitudinal axis and to each other.

Example 14

The device for blood oxygenation, as in the example 1A or 1B, or 2, or 3, or 4, provided that the membrane has straight capillaries instead of spiral capillaries, that is parallel to the longitudinal axis and to each other.

The device operates in the way that the gas mixture is fed through the gas mixture inlet opening from the installation supplying this mixture to the expansion tank, and further the gas mixture is fed from this tank to the openings in the chamber base to the capillaries, transported in the capillaries and discharged through the openings made in the opposite base to the gas mixture discharging tank, and further through the outlet opening to the outside of the device, and simultaneously blood cooled in the chamber is fed into the gas exchange chamber through the inlet opening, blood stream is transported along and in parallel to the longitudinal axis of the chamber and longitudinal axes of the capillaries, in which the gas mixture is transported, preferably in the counterflow to the direction of gas mixture transport in the capillaries, after which blood is discharged from the chamber through the outlet opening of blood stream and then heated in the heating module to the physiological temperature. The system ensuring parallel blood transport in the chamber, however in counterflow to the gas mixture transport in the capillaries, without the detriment to the oxygenation effectiveness, it is possible to decrease blood concentration in gas mixture, which will reduce oxidative stress for the cells, including in particular haemoglobin, which will prevent coagulation and increase in pressure and additionally reduce the risk of the capture (blocking) effect of drugs potentially transported in blood on the membrane, including in particular antibiotics (potential formation of thrombi on the membrane can lead to capture of drug particles on this element).

Preferably, blood in the oxygenator is transported in the counterflow to the gas mixture flow due to higher effectiveness of gas exchange, maintaining the possibly lowest oxidative stress. This enables maintenance of constant concentration of blood oxygen (diffusion-controlled process).

In the counterflow variant, the blood particle is transported in the same direction as oxygen particles, gas exchange takes place, however the efficiency is diffusion-controlled (limited). On the other had in the counterflow variant, due to continuous change in the contact phase—resulting from passing by of blood and oxygen particles—the process is not diffusion-controller and the process is not limited throughout the entire area of the oxygenator chamber by means of diffusion control. Blood particle that is still unsaturated, will be still able to bond with another batch of fresh oxygen and in effect of contact with another oxygen particles that pass by, will be able to absorb them. In addition, partial pressure at the contact point of blood particles with oxygen particles will be higher than in the co-current variant, which will enable more effective gas exchange. At sufficiently fast flow of gas mixture stream comprising oxygen, the effect of gas exchange will be additionally enhanced by the Venturi effect. Flowing blood sucks the oxygen particles from the capillary, even at relatively low pressure of gas mixture stream (does not require high oxygen pressure which is necessary in the oxygenator with blood flow perpendicular to the oxygen flow direction).

In the method known in the art, that is in the perpendicular variant (blood stream transported perpendicularly to the oxygen flow direction), the oxygen particles that penetrated the capillary micropores had a short contact with blood and required higher energy to disconnect the oxygen particle from the tube surface (required high energy expenditure or high oxygen concentration, that can lead to oxidative stress and impairment of haemoglobin cells). With regard to the above, blood oxygenation was uneven and bearing high oxidative stress.

In the method previously known in the art, blood in the oxygenator was transported perpendicularly to the oxygen transport direction in the capillaries, which resulted in changes to oxygen concentrations and the oxygenation was sinusoidal rather than linear, since the active surface of exchange was relatively lower (stepwise from one capillary to another), which forced the application of high oxygen concentration to achieve the same blood oxygenation rate as according to this invention.

We claim:

1. A device for blood oxygenation, with a membrane made of an organic material of blowing properties, comprising:

a gas exchange chamber having a longitudinal shape as a straight cylinder or a elliptic cylinder and being comprised of a first base on a first side of the longitudinal shape, a side wall, and a second base opposite said first base and on a second side of the longitudinal shape;

a first plurality of passage openings on said first base;

a second plurality of passage openings on said second base, an expansion tank being in gas-tight connection with said first side so as to feed a gas mixture containing oxygen to said gas exchange chamber and being comprised of an inlet opening being configured so as to provide the gas mixture from a feeding installation;

a gas mixture discharging tank being in gas-tight connection with said second side so as to transport the gas mixture from said gas exchange chamber and being comprised of an outlet opening being configured so as to transport the gas mixture from said gas exchange chamber;

a membrane being comprised of a capillary bundle and being uniformly distributed inside said gas exchange chamber, wherein said capillary bundle is comprised of a plurality of capillaries, each capillary of said plurality of capillaries being comprised of a semi-permeable material so as to be permeable to gas mixture particles and non-permeable to blood particles and having respective ends anchored in a corresponding passage opening of said first plurality of passage openings on said first base and a corresponding passage opening of said second plurality of passage openings on said second base, wherein each capillary of said plurality of capillaries is tensed with a tension force of a value from 1 to 100 N, wherein each capillary of said plurality of capillaries is parallel to the longitudinal axis of said gas exchange chamber and to each other, or each capillary of said plurality of capillaries is arranged spirally so as to be twisted along the longitudinal axis of said gas exchange chamber by an angle falling within a range from 15 to 720 degrees, wherein each capillary of said plurality of capillaries is comprised of a tube having an external diameter from 30 to 600 μm;

a blood flow inlet opening in said side wall at said first side of said gas exchange chamber; and a blood flow outlet opening in said side wall at said second side of said gas exchange chamber so as to flow a blood stream from said blood flow inlet opening to said blood flow outlet opening wherein each capillary of said plurality of capillaries is comprised of an organic material having blowing, anti-inflammatory and antithrombotic properties, wherein the organic material consists of:
  a base being at least one of a group consisting of: polytetrafluoroethylene (PTFE, teflon), polyvinylidene fluoride (PVDF), copolymer of hexafluoropropylene, and tetrafluoroethylene (FEP); and
  an admixture of albumin being embedded in a microstructure of a base material and having a base admixture ratio from 80÷1 to 1200÷1, said membrane being comprised of 40 to 60% open pores and a remaining 60-40% closed pores and being filled with an active substance being comprised of albumin; or
  an admixture of argatroban being embedded in said microstructure and having a corresponding base admixture ratio from 80÷1 to 1200÷1, said membrane being comprised of 40 to 60% open pores and a remaining 60-40% closed pores and being filled with a respective active substance being comprised of argatroban; or
  an admixture of bivalirudin being embedded in said microstructure and having a corresponding base admixture ratio from 80÷1 to 1200÷1, said membrane being comprised of 40 to 60% open pores and a remaining 60-40% closed pores and being filled with a respective active substance being comprised of bivalirudin; or
  an admixture of fondaparinux being embedded in said microstructure and having a corresponding base admixture ratio from 80÷1 to 1200÷1, said membrane being comprised of 40 to 60% open pores and a remaining 60-40% closed pores and being filled with a respective active substance being comprised of fondaparinux; or
  an admixture of heparin being embedded in said microstructure and having a corresponding base admixture ratio from 80÷1 to 1200÷1, said membrane being comprised of 40 to 60% open pores and a remaining 60-40% closed pores and being filled with a respective active substance being comprised of heparin.

2. The device for blood oxygenation, according to claim 1, further comprising:
  a blood stream cooler being connected to said blood flow inlet so as to be configured for cooling down by 0.5-3.5° C.; and
  a blood stream heating module being connected to said blood flow outlet so as to be configured for heating to a physiological blood temperature.

3. The device for blood oxygenation, according to claim 2, wherein said blood stream cooler is comprised of Peltier cells, or wherein said blood stream heating module is comprised of respective Peltier cells.

4. The device for blood oxygenation, according to claim 1, wherein said blood flow inlet is comprised of an opening placed near said gas mixture discharging tank, and wherein said blood flow outlet is comprised of an opening placed near said expansion tank.

5. The device for blood oxygenation, according to claim 1, wherein said first plurality of passage openings are arranged in equal distances from each other and symmetrically to each other on said first base, wherein said second plurality of passage opening are arranged in equal distances from each other and symmetrically to each other on said second base, and wherein said plurality of capillaries are arranged in equal distances from each other and symmetrically to each other according to said first plurality of passage openings and said second plurality of passage openings.

6. The device for blood oxygenation, according to claim 1, further comprising:
  a high efficiency particulate air (HEPA) filter assembled at said outlet opening of said gas mixture discharging tank.

7. The device for blood oxygenation, according to claim 1, wherein said blood flow inlet opening is at a distance not exceeding 5 mm from said first base, and wherein said blood flow outlet opening is at a distance not exceeding 5 mm from said second base.

8. The device for blood oxygenation, according to claim 1, wherein said blood flow inlet opening of blood stream is made at the is opposite side compared to the said blood flow outlet opening of blood stream, symmetrically to the chamber's centre of symmetry so as to be symmetrical across a center of said gas exchange chamber.

9. The device for blood oxygenation, according to claim 1, further comprising:
  two blood stream regulators being assembled on an inner surface of said gas exchange chamber and along a length of said gas exchange chamber from said expansion tank to said gas mixture tank, said two blood stream regulators being symmetrical across a center of said gas exchange chamber, wherein said two blood stream regulators are comprised of longitudinal notches, and wherein said longitudinal notches are parallel to the longitudinal axis of gas exchange chamber corresponding to each capillary of said plurality of capillaries being parallel to the longitudinal axis of said gas exchange chamber or rotated along the longitudinal axis of said gas exchange chamber corresponding to each capillary of said plurality of capillaries being spirally twisted along the longitudinal axis of said gas exchange chamber by a same angle falling within the range from 15 to 720 degrees.

10. The device for blood oxygenation, according to claim 1, wherein said blood flow outlet opening is assembled with densely woven fiber mesh or an identical material to said semi-permeable material of each capillary of said plurality of capillaries, said identical material having mesh holes from 15 to 100 μm and transverse to said plurality of capillaries.

11. The device for blood oxygenation, according to claim 1, wherein said blood flow inlet opening is assembled with densely woven fibre fiber mesh or a respective identical material identical as the capillary to said semi-permeable material of each capillary of said plurality of capillaries, said respective identical material in a way that the having respective mesh holes have the side from 15 to 100 μm and transverse to said plurality of capillaries.

12. The device for blood oxygenation, according to claim 1, further comprising:

a first blood flow outlet thrombus filter module connected to said blood flow outlet opening;

a second blood flow outlet thrombus filter module connected to said blood flow outlet opening; and a bypass connected to said first blood flow outlet thrombus filter module and said second blood flow outlet thrombus filter module so as to direct a blood stream to either said first blood flow outlet thrombus filter module or said second blood flow outlet thrombus filter module interchangeably.

13. The device for blood oxygenation, according to claim 1, further comprising:

a first blood flow outlet thrombus filter module connected to said blood flow outlet opening;

a second blood flow outlet thrombus filter module connected to said blood flow outlet opening; and a bypass connected to said first blood flow outlet thrombus filter module and said second blood flow outlet thrombus filter module so as to direct a blood stream to either said first blood flow outlet thrombus filter module or said second blood flow outlet thrombus filter module interchangeably.

14. The device for blood oxygenation, according to claim 12, further comprising:

a blood stream heating module being connected to said blood flow outlet so as to be configured for heating to a physiological blood temperature and being downstream from said bypass, said first blood flow outlet thrombus filter module and said second blood flow outlet thrombus filter module.

\* \* \* \* \*